US012661528B2

(12) United States Patent
Magaz et al.

(10) Patent No.: US 12,661,528 B2
(45) Date of Patent: Jun. 23, 2026

(54) PHANTOM SYSTEMS FOR RADIATION DOSIMETRY WITH REMOVABLE ATTACHMENTS

(71) Applicant: Sun Nuclear Corporation, Melbourne, FL (US)

(72) Inventors: Oscar Casares Magaz, Leon (ES); Mark Rose, Apopka, FL (US); Jeffrey Zack, Melbourne, FL (US); Jeffrey M. Kapatoes, Melbourne, FL (US)

(73) Assignee: SUN NUCLEAR CORPORATION, Melbourne, FL (US)

( * ) Notice: Subject to any disclaimer, the term of this patent is extended or adjusted under 35 U.S.C. 154(b) by 717 days.

(21) Appl. No.: 17/941,842

(22) Filed: Sep. 9, 2022

(65) Prior Publication Data

US 2023/0084185 A1 Mar. 16, 2023

Related U.S. Application Data

(60) Provisional application No. 63/244,136, filed on Sep. 14, 2021.

(51) Int. Cl.
*A61N 5/10* (2006.01)

(52) U.S. Cl.
CPC .......... *A61N 5/1075* (2013.01); *A61N 5/1049* (2013.01); *A61N 2005/1076* (2013.01)

(58) Field of Classification Search
CPC ................ A61N 5/1049; A61N 5/1075; A61N 2005/1076
See application file for complete search history.

(56) References Cited

U.S. PATENT DOCUMENTS

| | | | |
|---|---|---|---|
| 759,608 | A | 5/1904 | Harper |
| 1,239,145 | A | 9/1917 | Wantz |
| 2,818,510 | A | 12/1957 | Verse |
| 3,033,985 | A | 5/1962 | Petree |
| 3,267,728 | A | 8/1966 | Solomons |
| 3,327,213 | A | 6/1967 | Wald, Jr. |
| 3,394,258 | A | 7/1968 | Schleiger |
| 3,433,953 | A | 3/1969 | Sweet |
| 3,665,762 | A | 5/1972 | Domen |
| 3,783,251 | A | 1/1974 | Pavkovich |

(Continued)

FOREIGN PATENT DOCUMENTS

| | | |
|---|---|---|
| CA | 2718408 | 9/2009 |
| DE | 102009039345 A1 | 3/2011 |

(Continued)

OTHER PUBLICATIONS

Albers et al., CRC HAndbook of Chemistry and Physics, 87th Ed., Edited by R.C. Weast CRC, Cleveland, 1976. pp. F-11, D-171, E-6. (4 pages).

(Continued)

*Primary Examiner* — Blake C Riddick
(74) *Attorney, Agent, or Firm* — Pillsbury Winthrop Shaw Pittman, LLP

(57) ABSTRACT

A phantom system is disclosed that includes a phantom and at least one removable phantom attachment configured to be attached to the phantom so that the phantom system may have an orientation, location and/or anthropomorphic feature identifiable to an imaging device.

14 Claims, 10 Drawing Sheets

(56)                    References Cited

U.S. PATENT DOCUMENTS

| | | | |
|---|---|---|---|
| 3,790,794 A | 2/1974 | Murray | |
| 3,978,336 A | 8/1976 | Roux | |
| 3,980,885 A | 9/1976 | Steward | |
| 4,058,832 A | 11/1977 | Vagi | |
| 4,063,097 A | 12/1977 | Barrett | |
| 4,107,531 A | 8/1978 | Garratt | |
| 4,157,472 A | 6/1979 | Barrett | |
| 4,312,224 A | 1/1982 | Domen | |
| 4,450,440 A | 5/1984 | White | |
| 4,455,609 A | 6/1984 | Inamura | |
| 4,613,754 A | 9/1986 | Vinegar | |
| 4,638,502 A * | 1/1987 | Yaffe | G09B 23/286 |
| | | | 250/252.1 |
| 4,729,099 A | 3/1988 | Iverson | |
| 4,765,749 A | 8/1988 | Bourgade | |
| 4,777,442 A | 10/1988 | Rosenthal | |
| 4,871,914 A | 10/1989 | Simon | |
| 4,887,287 A | 12/1989 | Cobben | |
| 5,059,801 A | 10/1991 | Burgess | |
| 5,099,505 A | 3/1992 | Seppi | |
| 5,160,337 A | 11/1992 | Cosman | |
| 5,262,649 A | 11/1993 | Antonuk | |
| 5,388,142 A | 2/1995 | Morris | |
| 5,394,452 A | 2/1995 | Swerdloff | |
| 5,596,653 A | 1/1997 | Kurokawa | |
| 5,602,892 A | 2/1997 | Llacer | |
| 5,621,214 A | 4/1997 | Sofield | |
| 5,622,187 A | 4/1997 | Carol | |
| 5,627,367 A | 5/1997 | Sofield | |
| 5,635,709 A | 6/1997 | Sliski | |
| 5,640,436 A | 6/1997 | Kawai | |
| 5,652,430 A | 7/1997 | Lee | |
| 5,661,310 A | 8/1997 | Jones | |
| 5,704,890 A | 1/1998 | Bliss | |
| 5,712,482 A | 1/1998 | Gaiser | |
| 5,719,916 A * | 2/1998 | Nelson | A61B 6/583 |
| | | | 378/207 |
| 5,873,826 A | 2/1999 | Gono | |
| 5,988,875 A | 11/1999 | Gershfeld | |
| 6,038,283 A | 3/2000 | Carol | |
| 6,125,335 A | 9/2000 | Simon | |
| 6,131,690 A | 10/2000 | Galando | |
| 6,148,272 A | 11/2000 | Bergstrom | |
| 6,175,761 B1 | 1/2001 | Frandsen | |
| 6,207,952 B1 | 3/2001 | Kan | |
| 6,257,552 B1 | 7/2001 | Crow | |
| 6,261,219 B1 | 7/2001 | Meloul | |
| 6,301,329 B1 | 10/2001 | Surridge | |
| 6,322,249 B1 | 11/2001 | Wofford | |
| 6,345,114 B1 | 2/2002 | Mackie | |
| 6,364,529 B1 | 4/2002 | Dawson | |
| 6,398,710 B1 | 6/2002 | Ishikawa | |
| 6,466,644 B1 | 10/2002 | Hughes | |
| 6,516,046 B1 | 2/2003 | Stephan | |
| 6,535,574 B1 | 3/2003 | Collins | |
| 6,535,756 B1 | 3/2003 | Simon | |
| 6,552,347 B1 | 4/2003 | Dimcovski | |
| 6,560,311 B1 | 5/2003 | Shepard | |
| 6,594,336 B2 | 7/2003 | Nishizawa | |
| 6,609,626 B2 | 8/2003 | Young | |
| 6,609,826 B1 | 8/2003 | Fujii | |
| 6,626,569 B2 | 9/2003 | Reinstein | |
| 6,636,622 B2 | 10/2003 | Mackie | |
| 6,648,503 B2 | 11/2003 | Tanaka | |
| 6,668,073 B1 * | 12/2003 | Robar | G01T 1/169 |
| | | | 382/128 |
| 6,712,508 B2 | 3/2004 | Nilsson | |
| 6,788,759 B2 | 9/2004 | Op De Beek | |
| 6,799,068 B1 | 9/2004 | Hartmann | |
| 6,810,107 B2 | 10/2004 | Steinberg | |
| 6,810,108 B2 | 10/2004 | Clark | |
| 6,833,707 B1 | 12/2004 | Dahn | |
| 6,839,404 B2 | 1/2005 | Clark | |
| 6,853,702 B2 | 2/2005 | Renner | |
| 6,888,919 B2 | 5/2005 | Graf | |
| 6,904,119 B2 | 6/2005 | Oikawa | |
| 6,904,125 B2 | 6/2005 | Van Dyk | |
| 6,904,162 B2 | 6/2005 | Robar | |
| 6,974,254 B2 | 12/2005 | Paliwal | |
| 6,990,368 B2 | 1/2006 | Simon | |
| 6,992,309 B1 | 1/2006 | Petry | |
| 7,016,454 B2 | 3/2006 | Warnberg | |
| 7,065,812 B2 | 6/2006 | Newkirk | |
| 7,076,023 B2 | 7/2006 | Ghelmansarai | |
| 7,098,463 B2 | 8/2006 | Adamovics | |
| 7,116,749 B2 | 10/2006 | Besson | |
| 7,125,163 B2 | 10/2006 | Eigler | |
| 7,127,028 B2 | 10/2006 | Sendai | |
| 7,127,030 B2 | 10/2006 | Tamegai | |
| 7,142,634 B2 | 11/2006 | Engler | |
| 7,193,220 B1 | 3/2007 | Navarro | |
| 7,221,733 B1 | 5/2007 | Takai | |
| 7,233,688 B2 | 6/2007 | Ritt | |
| 7,234,355 B2 | 6/2007 | Dewangan | |
| 7,298,820 B2 | 11/2007 | Nelson | |
| 7,339,159 B2 | 3/2008 | Juh | |
| 7,349,523 B2 | 3/2008 | Jenkins | |
| 7,352,840 B1 | 4/2008 | Nagarkar | |
| 7,371,007 B2 | 5/2008 | Nilsson | |
| 7,386,089 B2 | 6/2008 | Endo | |
| 7,420,160 B2 | 9/2008 | Delaperriere | |
| 7,453,976 B1 | 11/2008 | Yin | |
| 7,455,449 B2 | 11/2008 | Nishimura | |
| 7,471,765 B2 | 12/2008 | Jaffray | |
| 7,515,681 B2 | 4/2009 | Ebstein | |
| 7,579,608 B2 | 8/2009 | Takahashi | |
| 7,605,365 B2 | 10/2009 | Chen | |
| 7,636,419 B1 * | 12/2009 | Nelson | A61N 5/1048 |
| | | | 378/65 |
| 7,668,292 B1 | 2/2010 | Bose | |
| 7,734,010 B2 | 6/2010 | Otto | |
| 7,750,311 B2 | 7/2010 | Daghighian | |
| 7,766,903 B2 | 8/2010 | Blumenkranz | |
| 7,773,723 B2 | 8/2010 | Nord | |
| 7,778,383 B2 | 8/2010 | Koehler | |
| 7,778,392 B1 | 8/2010 | Berman | |
| 7,778,680 B2 | 8/2010 | Goode, Jr. | |
| 7,782,998 B2 | 8/2010 | Langan | |
| 7,945,022 B2 | 5/2011 | Nelms | |
| 8,044,359 B2 | 10/2011 | Simon | |
| 8,093,549 B2 | 1/2012 | Navarro | |
| 8,130,905 B1 | 3/2012 | Nelms | |
| 8,136,773 B2 | 3/2012 | Schmutzer | |
| 8,147,139 B2 | 4/2012 | Papaioannou | |
| 8,218,718 B1 | 7/2012 | Van Herk | |
| 8,235,530 B2 | 8/2012 | Maad | |
| 8,242,458 B2 | 8/2012 | Rinecker | |
| 8,321,179 B2 | 11/2012 | Simon | |
| 8,325,878 B2 | 12/2012 | Mcnutt | |
| 8,430,564 B2 | 4/2013 | Simmons | |
| 8,457,713 B2 | 6/2013 | Kagermeier | |
| 8,474,794 B2 | 7/2013 | Liljedahl | |
| 8,536,547 B2 | 9/2013 | Maurer | |
| 8,541,756 B1 | 9/2013 | Treas | |
| 8,605,857 B1 | 12/2013 | Renner | |
| 8,632,448 B1 | 1/2014 | Schulte | |
| 8,726,814 B1 | 5/2014 | Matteo | |
| 8,794,899 B2 | 8/2014 | Cozza | |
| 8,833,709 B2 | 9/2014 | Weng | |
| 8,840,304 B2 | 9/2014 | Perez Zarate | |
| 8,840,340 B2 | 9/2014 | Eisenhower | |
| 8,874,385 B2 | 10/2014 | Takayanagi | |
| 8,927,921 B1 | 1/2015 | Nelms | |
| 9,050,460 B2 | 6/2015 | Hildreth | |
| 9,097,384 B1 | 8/2015 | Simon | |
| 9,310,263 B2 | 4/2016 | Thoen | |
| 9,463,336 B2 | 10/2016 | Nelms | |
| 9,480,861 B2 | 11/2016 | Kapatoes | |
| 9,561,388 B2 | 2/2017 | Hildreth | |
| 9,586,060 B2 | 3/2017 | Seuntjens | |
| 9,750,955 B2 | 9/2017 | Mcnutt | |
| 9,895,557 B2 | 2/2018 | Seuntjens | |
| 10,099,067 B2 | 10/2018 | Kapatoes | |
| 10,413,754 B2 | 9/2019 | Seuntjens | |

(56)                References Cited

U.S. PATENT DOCUMENTS

| | | | |
|---|---|---|---|
| 10,755,823 B2 | 8/2020 | Carette | |
| 2001/0042841 A1 | 11/2001 | Lyons | |
| 2002/0077545 A1 | 6/2002 | Takahashi | |
| 2002/0080912 A1 | 6/2002 | Mackie | |
| 2003/0043879 A1 | 3/2003 | Tanaka | |
| 2003/0043960 A1 | 3/2003 | Op De Beek | |
| 2003/0138077 A1 | 7/2003 | Lee | |
| 2003/0231740 A1 | 12/2003 | Paliwal | |
| 2004/0066880 A1 | 4/2004 | Oikawa | |
| 2004/0068182 A1 | 4/2004 | Misra | |
| 2004/0096033 A1 | 5/2004 | Seppi | |
| 2004/0113094 A1 | 6/2004 | Lyons | |
| 2004/0120560 A1 | 6/2004 | Robar | |
| 2004/0129888 A1 | 7/2004 | Kannan | |
| 2004/0158145 A1 | 8/2004 | Ghelmansarai | |
| 2004/0211917 A1 | 10/2004 | Adamovics | |
| 2004/0228435 A1 | 11/2004 | Russell | |
| 2004/0251419 A1 | 12/2004 | Nelson | |
| 2005/0013406 A1* | 1/2005 | Dyk | A61N 5/1049 |
| | | | 378/65 |
| 2005/0035282 A1* | 2/2005 | Lehmann | A61N 5/1048 |
| | | | 250/252.1 |
| 2005/0077459 A1 | 4/2005 | Engler | |
| 2005/0111621 A1 | 5/2005 | Riker | |
| 2005/0281389 A1 | 12/2005 | Kusch | |
| 2006/0002519 A1 | 1/2006 | Jenkins | |
| 2006/0033044 A1 | 2/2006 | Gentry | |
| 2006/0184124 A1 | 8/2006 | Cowan | |
| 2006/0203964 A1 | 9/2006 | Nyholm | |
| 2006/0203967 A1 | 9/2006 | Nilsson | |
| 2006/0266951 A1 | 11/2006 | Fritsch | |
| 2007/0041497 A1 | 2/2007 | Schnarr | |
| 2007/0041499 A1 | 2/2007 | Lu | |
| 2007/0053492 A1 | 3/2007 | Kidani | |
| 2007/0071169 A1 | 3/2007 | Yeo | |
| 2007/0081629 A1 | 4/2007 | Yin | |
| 2007/0086577 A1 | 4/2007 | Kobayashi | |
| 2007/0140413 A1* | 6/2007 | Saracen | A61B 6/4458 |
| | | | 378/207 |
| 2007/0172020 A1 | 7/2007 | Nambu | |
| 2007/0181815 A1 | 8/2007 | Ebstein | |
| 2007/0195930 A1 | 8/2007 | Kapatoes | |
| 2008/0031406 A1 | 2/2008 | Yan | |
| 2008/0049896 A1 | 2/2008 | Kuduvalli | |
| 2008/0049898 A1 | 2/2008 | Romesberg | |
| 2008/0091388 A1 | 4/2008 | Failla | |
| 2008/0103834 A1 | 5/2008 | Reiner | |
| 2008/0118137 A1 | 5/2008 | Chen | |
| 2008/0146914 A1 | 6/2008 | Polzin | |
| 2008/0260368 A1 | 10/2008 | Chang | |
| 2008/0267352 A1 | 10/2008 | Aoi | |
| 2008/0292055 A1 | 11/2008 | Boone | |
| 2008/0298553 A1 | 12/2008 | Takahashi | |
| 2009/0003512 A1 | 1/2009 | Pouliot | |
| 2009/0003528 A1 | 1/2009 | Ramraj | |
| 2009/0005671 A1 | 1/2009 | Kreischer | |
| 2009/0067576 A1 | 3/2009 | Maltz | |
| 2009/0090870 A1 | 4/2009 | Ahnesjo | |
| 2009/0175418 A1 | 7/2009 | Sakurai | |
| 2009/0190723 A1* | 7/2009 | Jang | A61B 6/5276 |
| | | | 378/207 |
| 2009/0217999 A1 | 9/2009 | Becker | |
| 2009/0227841 A1 | 9/2009 | Miyako | |
| 2009/0250618 A1 | 10/2009 | Simon | |
| 2009/0252292 A1 | 10/2009 | Simon | |
| 2009/0326365 A1 | 12/2009 | Goldenberg | |
| 2010/0008467 A1 | 1/2010 | Dussault | |
| 2011/0022360 A1 | 1/2011 | Simon | |
| 2011/0051893 A1 | 3/2011 | Mcnutt | |
| 2011/0085716 A1 | 4/2011 | Christophe | |
| 2011/0096906 A1 | 4/2011 | Langeveld | |
| 2011/0108702 A1 | 5/2011 | Jackson | |
| 2011/0158386 A1 | 6/2011 | Payne | |
| 2011/0204262 A1 | 8/2011 | Pu | |
| 2011/0210258 A1 | 9/2011 | Black | |
| 2011/0248188 A1 | 10/2011 | Brusasco | |
| 2011/0278444 A1 | 11/2011 | Navarro | |
| 2011/0306864 A1 | 12/2011 | Zarate | |
| 2012/0014618 A1 | 1/2012 | Sun | |
| 2012/0025105 A1 | 2/2012 | Brown | |
| 2012/0025826 A1 | 2/2012 | Zhou | |
| 2012/0097860 A1 | 4/2012 | Oguma | |
| 2012/0134471 A1* | 5/2012 | Krautim | A61N 5/1048 |
| | | | 378/65 |
| 2012/0230462 A1 | 9/2012 | Robar | |
| 2012/0292517 A1 | 11/2012 | Izaguirre | |
| 2012/0305793 A1 | 12/2012 | Schiefer | |
| 2012/0326057 A1 | 12/2012 | Remeijer | |
| 2013/0048869 A1 | 2/2013 | Kominami | |
| 2013/0048883 A1 | 2/2013 | Simon | |
| 2013/0119259 A1 | 5/2013 | Martin | |
| 2013/0258105 A1 | 10/2013 | Jozsef | |
| 2013/0267830 A1 | 10/2013 | Ojha | |
| 2013/0287170 A1 | 10/2013 | Ebstein | |
| 2013/0303902 A1 | 11/2013 | Smith | |
| 2014/0016754 A1 | 1/2014 | Sugiyama | |
| 2014/0064445 A1 | 3/2014 | Adler | |
| 2014/0073834 A1 | 3/2014 | Hildreth | |
| 2014/0077098 A1 | 3/2014 | Tachikawa | |
| 2014/0094642 A1 | 4/2014 | Fuji | |
| 2014/0105355 A1 | 4/2014 | Toimela | |
| 2014/0221816 A1 | 8/2014 | Franke | |
| 2014/0237213 A1 | 8/2014 | Gill | |
| 2014/0250480 A1 | 9/2014 | Koh | |
| 2014/0263990 A1 | 9/2014 | Kawrykow | |
| 2014/0316258 A1 | 10/2014 | Hahn | |
| 2015/0071408 A1 | 3/2015 | Ebstein | |
| 2015/0080634 A1 | 3/2015 | Huber | |
| 2015/0087879 A1 | 3/2015 | Nelms | |
| 2015/0108356 A1 | 4/2015 | Seuntjens | |
| 2015/0124930 A1 | 5/2015 | Verhaegen | |
| 2015/0238778 A1 | 8/2015 | Hildreth | |
| 2015/0283403 A1 | 10/2015 | Kapatoes | |
| 2015/0309193 A1 | 10/2015 | Kozelka | |
| 2015/0327825 A1 | 11/2015 | Suzuki | |
| 2015/0352376 A1 | 12/2015 | Wiggers | |
| 2016/0067479 A1 | 3/2016 | Marcovecchio | |
| 2016/0136460 A1 | 5/2016 | Baltes | |
| 2016/0155364 A1* | 6/2016 | Piron | G01R 33/58 |
| | | | 434/270 |
| 2016/0166857 A1 | 6/2016 | Nelms | |
| 2016/0256712 A1 | 9/2016 | Vahala | |
| 2016/0287906 A1 | 10/2016 | Nord | |
| 2016/0310762 A1 | 10/2016 | Ramezanzadeh Moghadam | |
| 2016/0354048 A1 | 12/2016 | Lee | |
| 2016/0361568 A1 | 12/2016 | Chappelow | |
| 2017/0021194 A1 | 1/2017 | Nelms | |
| 2017/0050052 A1* | 2/2017 | Burgett | B33Y 80/00 |
| 2017/0135580 A1 | 5/2017 | Lips | |
| 2017/0169734 A1* | 6/2017 | Wen | G09B 23/32 |
| 2017/0173367 A1 | 6/2017 | Seuntjens | |
| 2017/0177812 A1 | 6/2017 | Sjölund | |
| 2017/0225015 A1 | 8/2017 | Thieme | |
| 2017/0274225 A1 | 9/2017 | Baecklund | |
| 2018/0014798 A1 | 1/2018 | Beckman | |
| 2018/0028143 A1 | 2/2018 | Wiggers | |
| 2018/0028840 A1 | 2/2018 | Simon | |
| 2018/0043183 A1 | 2/2018 | Sheng | |
| 2018/0074143 A1 | 3/2018 | Delso | |
| 2018/0140272 A1 | 5/2018 | Ruchala | |
| 2018/0185672 A1 | 7/2018 | Ramezanzadeh Moghadam | |
| 2018/0243586 A1 | 8/2018 | Ramezanzadeh Moghadam | |
| 2018/0250529 A1 | 9/2018 | Seuntjens | |
| 2018/0250531 A1 | 9/2018 | Ansorge | |
| 2018/0344274 A1 | 12/2018 | Berr | |
| 2019/0014243 A1 | 1/2019 | Malone | |
| 2019/0118002 A1 | 4/2019 | Rosenwald | |
| 2019/0175951 A1* | 6/2019 | Yu | A61B 6/032 |
| 2019/0298285 A1 | 10/2019 | Rakic | |
| 2020/0061389 A1 | 2/2020 | Willcut | |
| 2020/0101327 A1 | 4/2020 | Alquist | |
| 2020/0253001 A1 | 8/2020 | Nauditt | |
| 2021/0011178 A1 | 1/2021 | Kapatoes | |
| 2021/0012507 A1 | 1/2021 | Kapatoes | |

(56)                    References Cited

U.S. PATENT DOCUMENTS

| | | | |
|---|---|---|---|
| 2021/0015441 A1 | 1/2021 | Bourne | |
| 2021/0220676 A1 | 7/2021 | Kawrykow | |
| 2021/0236856 A1 | 8/2021 | Kapatoes | |
| 2023/0330437 A1* | 10/2023 | Kerns | A61N 5/1075 |
| 2024/0091557 A1* | 3/2024 | Morcos | A61N 5/1016 |
| 2024/0115228 A1* | 4/2024 | Brown | A61N 5/1075 |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2400317 A1 | 12/2011 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| JP | 202035449 | 3/2020 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 A | 12/2013 |
| WO | 2015024360 | 2/2015 |
| WO | 2015073899 | 5/2015 |
| WO | 2016172352 | 10/2016 |
| WO | 2016200463 | 12/2016 |
| WO | 2019157249 A | 8/2019 |

OTHER PUBLICATIONS

Almond et al. In "AAPM TG-51 Protocol for Clinical Reference Dosimetry of High Energy Photon and Electron Beams", Med. Phys. VI, 26, pp. 1847-1870, 1999.

Aspen Aerogels, Pyrogel.RTM. 2250 Datasheet (Aspen Aerogels, Inc., Northborough, 2010). 2 pages.

Berlyand et al., "Portable Calorimeter for Measuring Absorbed Doses of X-Rays and Electrons from Accelerators", translated from Izeritel'naya Teknika, No. 11, Nov. 1991, pp. 56-58.

Boutillon in "Gap Correction for the Calorimetric Measurement of Absorbed Dose in Graphite with a 60Co Beam", Phys. Med. Biol., vol. 34, pp. 1809-1821, 1989.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (Dec. 1, 2011), XP020229547, 5 pages.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

Domen, "Absorbed Dose Water Calorimeter", (Med. Phys., vol. 7, 1980, pp. 157-159).

Duane et al., "An Absorbed Dose Calorimeter for IMRT Dosimetry", Metrologia, vol. 49, No. 5, 2012, pp. S168-S173.

Iaea, TRS., "398. Absorbed Dose Determination in External Beam Radiotherapy: An International Code of Practice for Dosimetry based on Standards of Absorbed Dose to Water," Vienna International Atomic Energy Agency (2000). 242 pages.

J. Seuntjens and S. Duane, "Photon absorbed dose standards," Metrologia 46, S39-S58 (2009).

Kawrakow et al. In "The EGSnrc Code System: Monte-Carlo Simulation of Electron and Photon Transport" (Canadian National Research Center, NRC Report PIRS-701, 2006.

Mc Ewen at al., 'A Portable Calorimeter for Measuring Absorbed Dose in the Radiotherapy Clinic', Physics in Medicine and Biology, vol. 45, No. 12, Dec. 2000, pp. 3675-3691.

Mcdonald et al., "Portable Tissue Equivalent Calorimeter", Medical Physics, vol. 3, 2, Mar.-Apr. 1976, pp. 80-86.

Mcewen et al., "Portable Graphite Calorimeter for Measuring Absorbed Dose in the Radiotherapy Clinic", Standards and Codes of Practice in Medical Radiation Dosimetry, IAEA-CN-96-9P,2002, pp. 115-121.

Miller, "Polystyrene Calorimeter for Electron Beam Dose Measurements", Radiation Physics Chemistry vol. 46, No. 4-6, Aug. 1995, pp. 1243-1246.

Myers et al., "Precision Adiabatic Gamma-Ray Calorimeter using Thermistor Thermometry", Review of Scientific Instruments, vol. 32, No. 9, Sep. 1961, pp. 1013-1015.

Nutbrown et. "Evaluation of Factors to Convert Absorbed Dose Calibrations in Graphite to Water for Mega-Voltage Photon Beams" (UK National Pysical Laboratory, NPL Report CIRM 37, 2000. 45 pages.

Ostrowsky et al., "The Construction of the Graphite Calorimeter GR9 at LNE-LNHB (Geometrical and technical considerations)", Report CEA-R-6184, 2008, 52 pages.

Owen et al "Correction for the Effect of the Gaps around the Core of an Absorbed Dose Graphite Calorimeter in High Energy Photon Radiation" (Phys. Med. Biol., vol. 36, pp. 1699-1704, 1991.

Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.

Petree et al., "A Comparison of Absorbed Dose Determinations in Graphite by Cavity Ionization Measurements and by Calorimetry", Journal of Research of the National Bureau of Standards-C. Engineering and Instrumentation. vol. 71 C, No. 1, Jan.-Mar. 1967, pp. 19-27.

Picard et al., "Construction of an Absorbed-Dose Graphite Calorimeter", Report BIPM-09/01' May 2009, 12 pages.

R. Alfonso et al., 'A new formalism for reference dosimetry of small and nonstandard fields,' Med. Phys. 35, 5179-5186 (2008).

Renaud et al., "Development of a graphite probe calorimeter for absolute clinical dosimetry", Med. Phvs., (Jan. 9, 2013), vol. 40, No. 2, p. 020701, XP012170941, 6 pages.

Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.

Ross et al. In "Water Calorimetry for Radiation Dosimetry" (Phys. Med. Biol., 1996, vol. 41, pp. 1-29).

S. Picard, D. T. Burns, and P. Roger, "Determination of the specific heat capacity of a graphite sample using absolute and differential methods," Metrologia 44, 294-302 (2007).

Sander et al., "NPL's new absorbed dose standard for the calibration of HDR 192Ir brachytherapy sources," Metrologia 49, S184-S188 (2012).

Seuntjens et al., Review of Calorimeter Based Absorbed Dose to Water Standards, Standards and Codes of Practice in Medical Radiation Dosimetry, IAEA-CN-96-3, 2002 p. 37-66.

Stewart in "The Development of New Devices for Accurate Radiation Dose Measurement: A garded Liquid Ionization Chamber and an Electron Sealed Water Calorimeter" Ph. D. Dissertation McGill University, 2007.

Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.

(56) References Cited

OTHER PUBLICATIONS

Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Brusasco, C, et al. 'A Dosimetry System for Fast Measurement of 3D Depth-dose Profiles in Charged-particle Tumor Therapy with Scanning Techniques.' Nuclear Instruments & Methods In Physics Research, Section-B: Beam Interactions With Materials and Atom 168.4 (2000): 578-92.
PCT App. No. PCT/US2015/024360; International Search Report and Written Opinion mailed Oct. 8, 2015. 13 page.
PCT App. No. PCT/US2015/024360; International Preliminary Report on Patentability Chapter I mailed Oct. 4, 2016. 9 pages.
Nelms, Benjamin. "Variation in External Beam Treatment, Plan Quality: An Inter-institutional Study of Planners and Planning Systems." Practical Radiation Oncology 2.4 (2012): 296-305.
PCT App. No. PCT/US2014/065808; International Search Report and Written Opinion mailed May 21, 2015. 9 pages.
PCT App. No. PCT/US2014/065808; International Preliminary Report on Patentability Chapter I mailed May 17, 2016. 7 pages.
Mackie et al., "Photon Beam Dose Computations", Proceedings of the 1996 AAPM Summer School, 1996. 36 pages.
PCT App. No. PCT/US2012/058345; International Search Report mailed Apr. 17, 2013. 3 pages.
Ahnesjo et al., "Calculation and Application of Point Spread Functions for Treatment Planning with High Energy Photon Beams", Acta. Oncol., 26, 49-56, 1987.
PCT App. No. PCT/US2012/058345; International Preliminary Report on Patentability Chapter I mailed Apr. 1, 2014. 5 pages.
PCT App. No. PCT/US2012/058345; International Written Opinion of the International Search Authority mailed Mar. 29, 2014. 4 pages.
Ahnesjo et al., "Dose calculations for external photon beams in radiotherapy", Phys. Med. Biol. 44, R99-R155 1999.
Ahnesjo, "Collapsed Cone Convolution of Radiant Energy for Photon Dose Calculation in Heterogeneous Media", Med. Phys. 16, 577-92, 1989.
Amanatides et al., "A Fast Voxel Traversal Algorithm for Ray Tracing", Eurographics '87, Conference Proceedings, 1987, 10 pages.
International Search Report and Written Opinion mailed Sep. 1, 2023, PCT Application No. PCT/iB/2023/055991.
Liu et al., "Correcting kernel tilting and hardening in convolution/superposition dose calculations for clinical devergent and polychomatic photon beams", Med. Phys. 24, 1729-1741, 1997.
Lu et al., "Accurate convolution/superposition for multi-resolution dose calculation using cumulative tabulated kernels", Phys. Med. Biol. 50, 655-680, 2005.
Mackie et al., The Use of Comp. In Rad. Ther., 107-110 1987.
Mackie et al., "Generation of Photon Energy Deposition Kernels Using the EGS Monte Carlo Code," 1988, Phys. Med. Biol. 33, pp. 1-20.
Mackie et al., "A convolution method of calculating dose for 15-MVx rays", Med. Phys. 12, 188-196, 1985.
Mohan et al., "Energy and angular distributions of photons from medical linear accelerators", Med. Phys. 12, 592-597, 1985.
Otto, "Volumetric modulated arc therapy: IMRT in a single gantry arc", Med. Phys. 35, 310-317, 2008.
Papanikolaou et al., "Investigation of the convolution method for polyenergetic spectra", Med. Phys. 20, 1327-1336, 1993.
Williams, "Pyramidal Parametrics", SIGGRAPH Comput. Graph. 17, 3, 1-11, 1983.
Yan et al., "Adaptive radiation therapy", Phys. Med. Biol. 42, 123-132, 1997.
Yu, "Intensity-modulated arc therapy with dynamic multileaf collimation: an alternative to tomotherapy", Phys. Med. Biol. 40, 1435-1449, 1995.

PCT App. No. PCT/US2009/043341; International Search Report mailed Jan. 5, 2010. 3 pages.
PCT App. No. PCT/US2009/043341; Written Opinion of the International Search Authority mailed Nov. 8, 2010. 3 pages.
PCT App. No. PCT/US2009/043341; International Preliminary Report on Patentability Chapter I mailed Nov. 9, 2010. 4 bages.
PCT App. No. PCT/US2012/053440; International Search Report and Written Opinion mailed Mar. 26, 2014. 3 pages.
"Waterphantom Dosimetry"; Medical Physics, vol. 3, May/Jun. 1976; p. 189.
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
PCT App. No. PCT/US2010/042680; International Search Report mailed Jan. 27, 2011. 2 pages.
PCT App. No. PCT/US2010/042680; International Written Opinion mailed Jan. 23, 2012. 8 pages.
PCT App. No. PCT/US2010/042680; International Preliminary Report on Patentability Chapter I mailed Jan. 24, 2012. 9 pages.
EP2457237 Supplemental European Search Report and Written Opinion mailed Mar. 8, 2017, 10 pages.
PCT App. No. PCT/US2009/036775; International Search Report mailed Nov. 12, 2009, 2 pages.
PCT App. No. PCT/US2009/036775; International Preliminary Report on Patentability Chapter II and Written Opinion mailed Sep. 12, 2010, 12 pages.
EP2277353 Search Report mailed Jul. 21, 2017, 10 pages.
Benedick Fraass; "Quality Assurance for Clinical Radiotherapy Treatment Planning," Med Phys., 25(10), Oct. 1998; pp. 1773-1829.
G.J. Kutcher; "Comprehensive AQ for Radiation Oncology Report;" AAPM Radiation Therapy Committee Task Group 40; Med. Phys., 21; Apr. 1994; pp. 581-618.
MapCheck and EPIDose; www.sunnuclear.com; manufactured by Sun Nuclear Corp.; Melbourne, FL; 2010, 8 pages.
MapCALC; www.sunnuclear.com; manufactured by Sun Nuclear Corp.; Melbourne, FL; 2009, 2 pages.
Joseph O. Deasy; "A Computational Environment for Radiotherapy Research," Med. Phys. 30, (5), May 2003; pp. 979-985.
Robert M. Eisberg; "Fundamentals of Modern Physics," Chapter 9—Perturbation Theory; John Wiley & Sons; 1967; pp. 268-272.
CYBERKNIFE; Cyberknife Systems; "The Standard of Radiosurgery", by Accuracy, Sunnyvale, CA; 2009; pp. 1-6.
"HI-ART"; www.tomotherapy.com; TomoTherapy, Madison, WI; 2007; pp. 1-8.
"Rapid Arc"; Varian Medical Systems, Inc., Palo Alto, CA; www.varian.com; 2007; pp. 1-8.
"VMAT"; Elekta, Ltd., Crawley UK; Document No. 4513 3710770; Oct. 8, 2008, 8 pages.
D.W.O. Rogers; "Montey Carlo Techniques in Radiotherapy," Physics in Canada, Medical Physics Special Issue, v. 58 #2; 2002; pp. 63-70.
T.R. Mcnutt, T.R. Mackie, P. J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 32(2); Feb. 2007; pp. 201-201.
PCT App. No. PCT/US2009/036917; International Search Report mailed Sep. 17, 2009. 2 pages.
PCT App. No. PCT/US2009/036917; Written Opinion mailed Sep. 12, 2010. 4 pages.
PCT App. No. PCT/US2009/036917; International Preliminary Report on Chapter II Patentability mailed Mar. 15, 2011. 3 bages.
PCT/US2017/044472; International Search Report and Written Opinion of the International Searching Authority, or the Declaration mailed Oct. 13, 2017. 12 pages.
PCT App. No. PCT/US2012/053440; International Preliminary Report on Patentability Chapter I mailed Mar. 3, 2015. 8 pages.

(56)                    References Cited

OTHER PUBLICATIONS

PCT App. No. PCT/US2016/028664; International Preliminary Report on Patentability mailed Nov. 2, 2017. 5 pages.

PCT App. No. PCT/US2017/062608; International Search Report and Written Opinion mailed Feb. 22, 2018. 11 pages.

McEwen et al.; "A portable calorimeter for measuring absorbed dose in radiotherapy clinic"; Dec. 2000; Phys. Med. Biol., vol. 45; pp. 3675-3691.

McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.

Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.

PCT App. No. PCT/US2018/020320; International Search Report and Written Opinion mailed Jul. 24, 2018. 18 pages.

Linacre, J.K. , "Harwell Graphite Calorimeter", IAEA, vol. 47, 1970 (pp. 46-54.).

PCT App. No. PCT/US2018/020320; International Preliminary Report on Patentability Chapter I mailed Sep. 12, 2019. pp. 1-11.

PCT Appl. No. PCT/US2018/056568; International Preliminary Report on Patentability, mailed Apr. 30, 2020. 8 pages.

International Search Report and Written Opinion mailed Oct. 2, 2020, PCT Application No. PCT/US2020/041458.

International Search Report and Written Opinion mailed Nov. 24, 2021, PCT Application No. PCT/IB2021/057573.

Jaccard, Maud, et al. "High dose-per-pulse electron beam dosimetry: commissioning of the Oriatron eRT6 prototype linear accelerator for preclinical use." Medical physics 45.2 (2018): 863-874. (Year: 2018).

Barthe, Jean. "Electronic dosimeters based on solid state detectors." Nuclear Instruments and Methods in Physics Research Section B: Beam Interactions with Materials and Atoms 184.1-2 (2001): 158-189. (Year: 2001).

\* cited by examiner

530

522

524

510

520

150

530

522

524

510

520

150

530

720
710
150

720
710
150

PHANTOM SYSTEMS FOR RADIATION DOSIMETRY WITH REMOVABLE ATTACHMENTS

RELATED APPLICATION(S)

This application claims priority to and the benefit of U.S. Provisional Application No. 63/244,136, filed Sep. 14, 2021, titled "Phantom Systems For Radiation Dosimetry," which is hereby incorporated by reference.

DESCRIPTION OF RELATED ART

Image-guided Radiotherapy (IGRT) utilizes imaging of a patient to locate, track, and treat regions of interest (e.g., tumors) with radiation. Imaging is performed a) before treatment delivery, to guide radiation treatment plan development, b) during patient setup, and c) during treatment, to guide and modify treatment delivery due to patient changes or movements (e.g., breathing). Imaging types can include Magnetic Resonance Imaging (MRI), single-image or Computed Tomography (CT), MV/kV X-Rays, ultrasound, infrared, optical, surface imaging, etc. Techniques such as PET, MRI and X-Rays are frequently used to image internal anatomy. Other techniques, described below, can monitor the external surface of a patient and be used to infer where regions of interest are currently located.

Surface-Guided Radiotherapy (SGRT) uses non-radiographic images to detect the patient's position during radiotherapy (RT). SGRT applies to a wide variety of techniques and solutions which, for example, detect surfaces of the patient in real time, compare with reference positions (e.g., from previous fractions or planning images) and trigger a radiation delivery hold when the patient's position is outside of defined thresholds.

SGRT-based techniques have increased significantly in the last decade and can be applied to multiple tumor locations with varying treatment modalities (e.g., Deep Inspiration Breath Hold (DIBH), Stereotactic Radiosurgery (SRS), Stereotactic Body Radiation Therapy (SBRT), and gated-RT). SGRT-based clinical protocols have showed increased patient safety and improved clinical outcomes.

Internal imaging used with radiation therapy can include techniques such as kV planar, MV planar, PET, MRI, or CT imaging to guide the delivery of radiation treatment. The imaging can occur intermittently along with imaging used to periodically check the location of patient anatomy or can be performed simultaneously with radiation delivery to allow real-time adjustments or gating of radiation beams during treatment.

SUMMARY

Phantom systems, associated components and their uses in, for example, radiation therapy quality assurance (QA) are disclosed. The phantom system can include a phantom and a removable phantom attachment configured to be attached to the phantom so that the phantom system has an identifiable orientation and/or location to an imaging device.

In some variations, the removable phantom attachment includes an external and/or internal anthropomorphic feature at least partially formed of a material having a density approximating water, tissue, bone, or air. The removable phantom attachment can be configured to be attached outside of the phantom and include an external anthropomorphic feature such as a nose, an ocular cavity, a mouth, a cranium, or an externally-visible portion of a clavicle, a pelvis, or a vertebrae. The removable phantom attachment may also include an internal anthropomorphic feature such as a nasal structure, ocular structure, or a mouth/throat structure.

In other variations, the removable phantom attachment can be an anthropomorphic sheath configured to cover at least a portion of the phantom and include an external and/or internal anthropomorphic feature.

In still other variations, the phantom can include a cavity and the removable phantom attachment can be configured to be inserted into the cavity. The removable phantom attachment can include at least one internal anthropomorphic feature able to be imaged by a kV or MV X-ray system, a CT system, an MM system.

In some variations, the removable phantom attachment can include an external or internal anthropomorphic feature having a size or shape corresponding to what the external or internal at anthropomorphic feature would be on a child. In other variations, a surface of the removable phantom attachment can have a diffuse reflectivity of between 0.1 and 0.8 for light of wavelengths between 400 nm and 700 nm.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

In IGRT, various imaging modalities can be utilized to monitor a patient before and during treatment, and adjust, adapt, or stop treatment delivery as needed based on patient motion or other changes in the patient's anatomy. One particular type of IGRT is Surface-Guided Radiation Therapy (SGRT). In SGRT, a patient's surface (e.g., their chest) can be monitored by a camera or other sensing device to detect and analyze patient movement. Because the movement of a patient's internal anatomy is often correlated to movement of the patient's surfaces, the delivery of radiation can be altered or stopped if such movement indicates that the target (e.g., a tumor) likely moved.

Other types of image guided radiation therapy perform similar functions but utilizing internal imaging of the patient. For example, PET, an MRI, CT or x-ray imaging device can monitor a patient's internal anatomy while treatment is being delivered. Based on such internal monitoring, radiation delivery can similarly be altered or stopped.

Quality Assurance for IGRT (either based on internal anatomy or based on a patient's surface features) can be performed to determine that an expected amount of radiation is delivered from a treatment device to a target location. IGRT-specific QA tests can use water or other tissue-equivalent materials, placed in the path of the radiation beam, that hold or support a radiation detector utilized to verify that an expected dose reaches the radiation detector through the materials. These materials are often incorporated into devices referred to as phantoms.

Figures 1A, 1B:
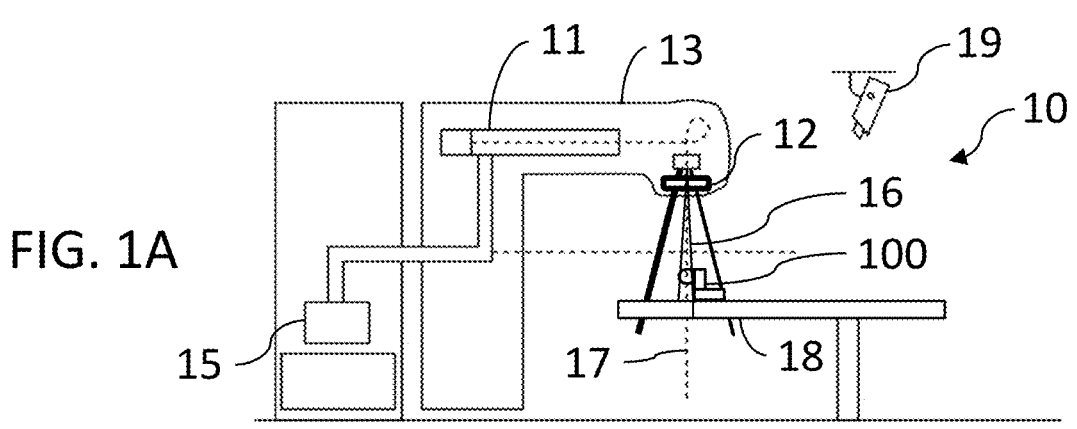
FIG. 1A is a diagram illustrating a simplified view of an exemplary radiation therapy system along with a phantom system for quality assurance in accordance with certain aspects of the present disclosure.
FIG. 1B is a diagram illustrating a simplified perspective view of an exemplary phantom for use with an SGRT system in accordance with certain aspects of the present disclosure.

FIG. 1A depicts an exemplary radiation delivery system 10 and an exemplary phantom system 100 for use in radiotherapy quality assurance. The exemplary radiation delivery system is an open (or "C-arm") type system, but other radiation delivery systems can include, for example, ring gantry-mounted radiation sources, robotic arm mounted radiation sources, etc. The exemplary radiation delivery system shown in FIG. 1A includes a linear accelerator (e.g., element 11 in FIG. 1A) working with an RF source 15, a collimator 12, and a rotatable gantry 13. In this exemplary system, the linear accelerator and collimator are mounted within the rotatable gantry to allow radiation 16 to be delivered along beam axis 17 at multiple angles to a patient resting on patient couch 18. While FIG. 1A depicts one example of a radiation delivery system, any type or configuration of a radiation delivery device is contemplated as usable with the embodiments disclosed herein. The exemplary system depicted in FIG. 1A also includes a simplified depiction of an SGRT system having an imaging device 19 such as a camera (e.g., visible light or infrared). Alternatively or additionally, internal imaging devices are contemplated to be used with the disclosed embodiments, for example, internal imaging utilizing a PET scanner, a kV or MV x-ray system, a CT system, an MM system, etc.

The technologies of the present disclosure can be used with radiation systems such as the exemplary system depicted in FIG. 1A, as well as with other types of radiotherapy systems such as collimated cobalt-60 sources, proton beams, heavy ion beams, etc. Any of these radiotherapy devices can be utilized with the systems of the present disclosure for assessing radiotherapy to a patient's body (e.g., chest, pelvis, neck, etc.) as well as to a patient's head.

FIG. 1B is a diagram illustrating a simplified perspective view of an exemplary phantom that may be used in accordance with certain aspects of the present disclosure. As shown, some implementations of phantom system 100 can include a phantom 110 and phantom support 120. Phantom support 120 can be adjustable and/or anchorable and can rigidly and precisely locate the phantom at a particular location relative to the radiation delivery system. For example, phantom support 120 can be configured to fix phantom 110 to patient couch 18 in order to measure radiation at and around the radiation delivery system isocenter.

Various radiation detectors 140 can be implemented with any of the disclosed phantom systems. Radiation detector 140 can be a two-dimensional array of radiation detectors configured to be inserted into the phantom. For example, one type of radiation detector can be a high-resolution 2D diode array that can be utilized in conjunction with quality assurance for stereotactic radiosurgery (SRS). Other types of radiation detectors can be film, 3D detector arrays, ionization chambers, etc.

In FIG. 1B, radiation detector 140 is depicted as partly outside of phantom 110 and partly inside phantom 110. As will be shown in later figures, phantom 110 has an internal space configured to receive radiation detector 140 into position for use in quality assurance. The active measurement area of radiation detector 140 is inside the phantom 110.

A phantom system can be configured to detect radiation 16 from various angles (depicted in FIG. 1B by the two arrows illustrating delivery of radiation 16 from two different angles). As shown in FIG. 1B, some implementations of a phantom 110 may be symmetric, such that they appear substantially the same regardless of the angular viewpoint around phantom axis 112. During quality assurance checks of SGRT, for example, gating checks or other QA functions may be performed that are dependent on viewing an angle of the patient (for example, testing the functionality of a system to gate off radiation delivery when a patient twists or rotates on the patient couch). For symmetric phantoms, as illustrated by the example in FIG. 1B, it may be difficult or impossible for an imaging device 19 to assess the angular position of the phantom because the phantom may look the same at any angle. Various implementations of the disclosed subject matter herein address such technical challenges, among others.

Figures 1C, 1D:
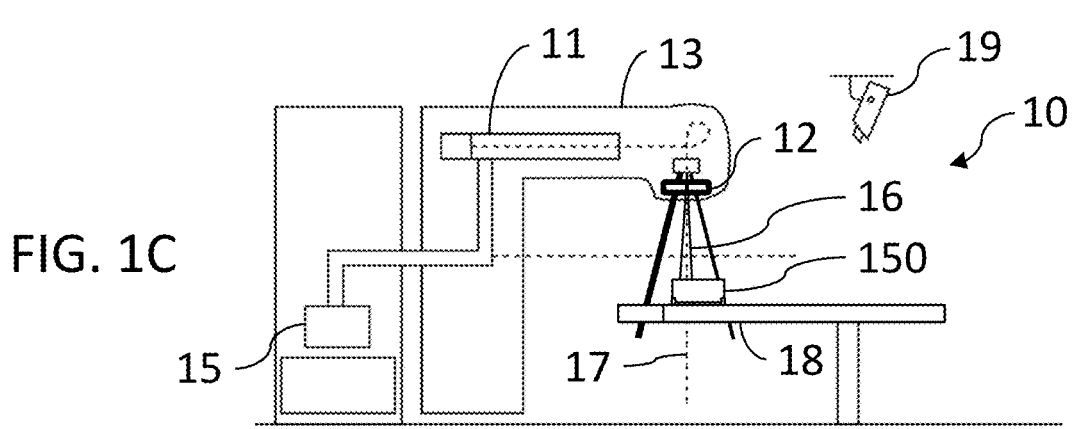
FIG. 1C depicts an exemplary radiation delivery system with a second embodiment of a phantom in a phantom system for use in radiotherapy quality assurance in accordance with certain aspects of the present disclosure.
FIG. 1D is a diagram illustrating a simplified perspective view of the exemplary second embodiment of the phantom in accordance with certain aspects of the present disclosure.

FIG. 1C depicts an exemplary radiation delivery system 10 with a second embodiment of a phantom 150 in phantom system 100 for use in radiotherapy quality assurance. FIG. 1D is a diagram illustrating a simplified perspective view of the exemplary second embodiment of the phantom. Phantom system 100 can have other types of phantoms besides the sort depicted in FIGS. 1A/B. The example phantom 150 depicted in FIGS. 1C/D can be a longer cylindrical model that may be better suited for simulating body (e.g., torso, pelvic, etc.) regions rather than the head. As such, various phantoms can be utilized that may be especially well-suited for performing, for example, QA on SRS systems (FIG. 1A/B) or SBRT (Stereotactic Body Radiation Therapy) systems (FIG. 1C/D), though these phantoms or any others may be used with the disclosed apparatuses and with any modes of radiation delivery/imaging. As used herein, when reference is made to phantom system 100 such contemplates that any phantom may be used, though for illustrative purposes a particular example may depict a specific sort of phantom.

A phantom system that includes a phantom, e.g., phantom 110 or 150, can also include one or more removable phantom attachments configured to be attached to the phantom so that the phantom system has an identifiable orientation and/or location to an imaging device (e.g., as shown in FIG. 1B). In some embodiments, the removable phantom attachment can include external and/or internal anthropomorphic feature(s) at least partially formed of a material having a density approximating, for example, water, tissue, bone, lung, or air. Some embodiments may also include materials visible to magnetic resonance imaging systems (e.g., MR signal generating materials mimicking fluids, fatty material, etc.). Other embodiments may similarly include materials visible to positron-electron tomography (PET) systems (e.g., radioactive tracer material), etc.

Such removable phantom attachments may not only provide spatial reference points to be detected by an imaging device, but may also improve the accuracy of delivered radiation measurements by approximating patient anatomical structures and their scattering/absorption of radiation dose.

Anatomically accurate phantoms further enable the end-to-end QA of radiotherapy systems. Such end-to-end QA may include putting the phantom through all of the steps that a patient would undergo, utilizing the same equipment. An example of an end-to-end test can include imaging the phantom, determining a radiation therapy plan to deliver dose to the phantom, locating the phantom in the actual treatment system, delivering radiation to the phantom as planned (gating or adapting delivery as guided by internal/external imaging), measuring the dose delivered to the phantom and comparing with the radiation treatment plan.

The term "anthropomorphic feature" as used herein refers to an object having the shape of at least a portion of a real patient's anatomy. Thus, an "anthropomorphic feature" can include external features such as ocular cavities, a nose, a mouth, clavicles, etc., internal features such as vertebrae, pelvic bones, ribs, etc., and overall patient surface shapes such as the overall shape of a head, a thorax, the pelvic region, etc.

The anthropomorphic features of the present disclosure may be attached to the outside of a phantom or may be attached by insertion into a phantom. As used herein, an external anthropomorphic feature is one that is at least partially visible on the outside of a patient (e.g., nose, lips, ears, the externally-visible portion of clavicle, etc.). An internal anthropomorphic feature (e.g., spine, cranium, etc.) is one that typically requires penetrating imaging (e.g., x-ray or MRI) to be fully visualized.

Figure 7A:
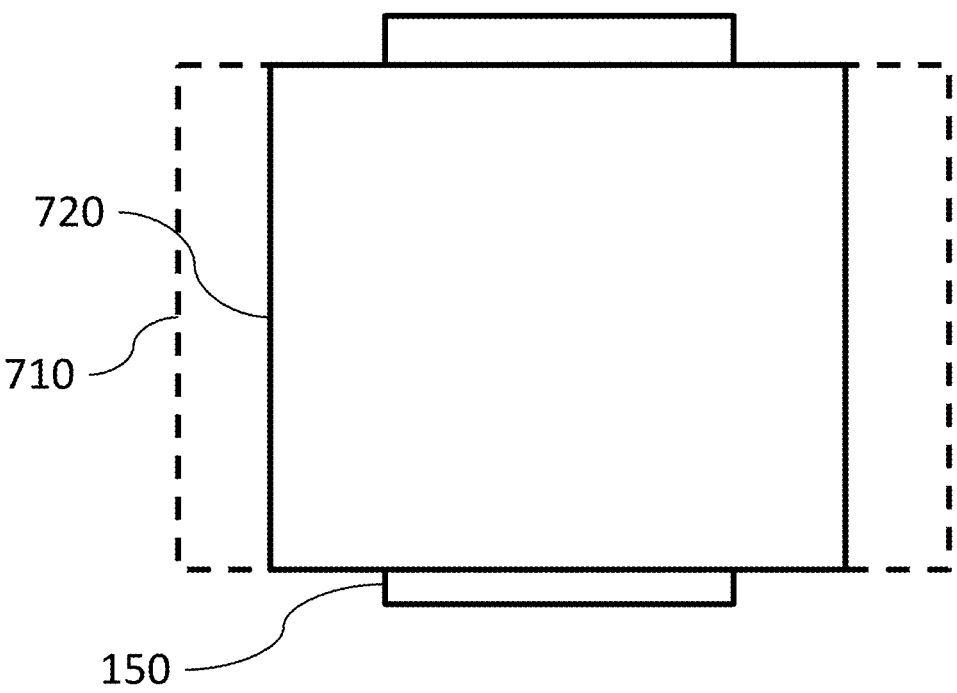
FIG. 7A is a diagram illustrating a simplified top view of an exemplary removable phantom attachment representing a change in patient weight in accordance with certain aspects of the present disclosure.
Figure 7B:
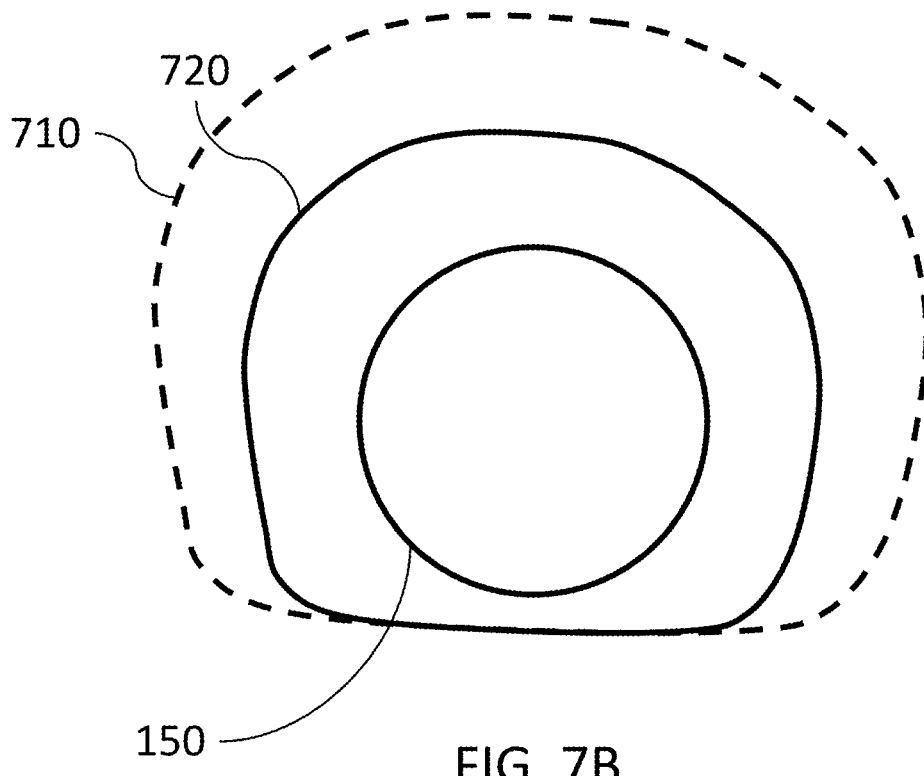
FIG. 7B is a diagram illustrating a simplified sectional view of the removable phantom attachment of FIG. 7A in accordance with certain aspects of the present disclosure.
Figure 7C:
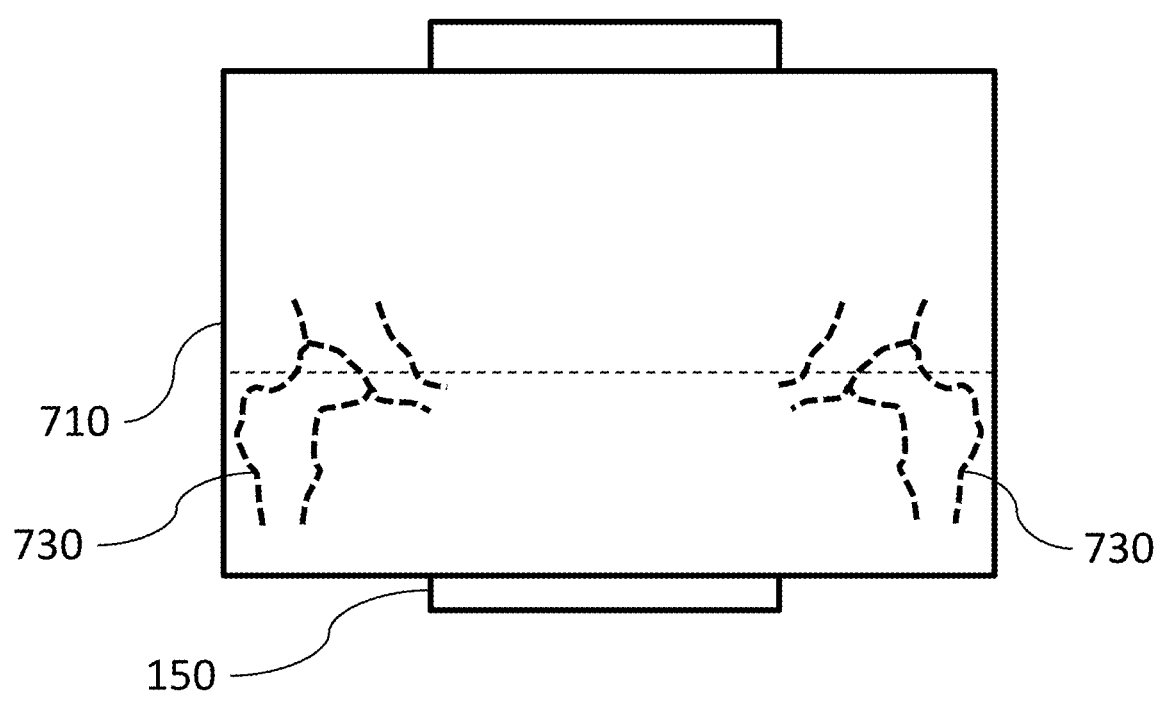
FIG. 7C is a diagram illustrating a simplified top view of an exemplary removable phantom attachment that includes an internal anthropomorphic feature in accordance with certain aspects of the present disclosure.
Figure 7D:
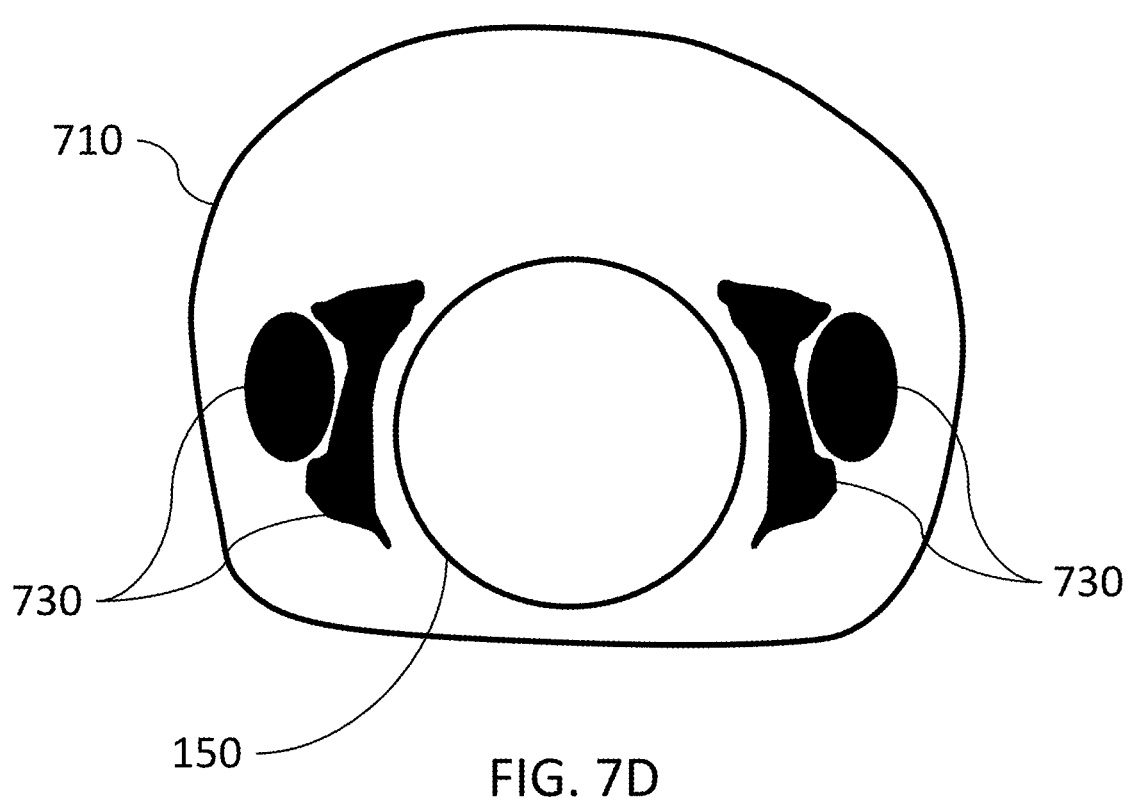
FIG. 7D is a diagram illustrating a simplified sectional view of the removable phantom attachment of FIG. 7C in accordance with certain aspects of the present disclosure.
Figure 8:
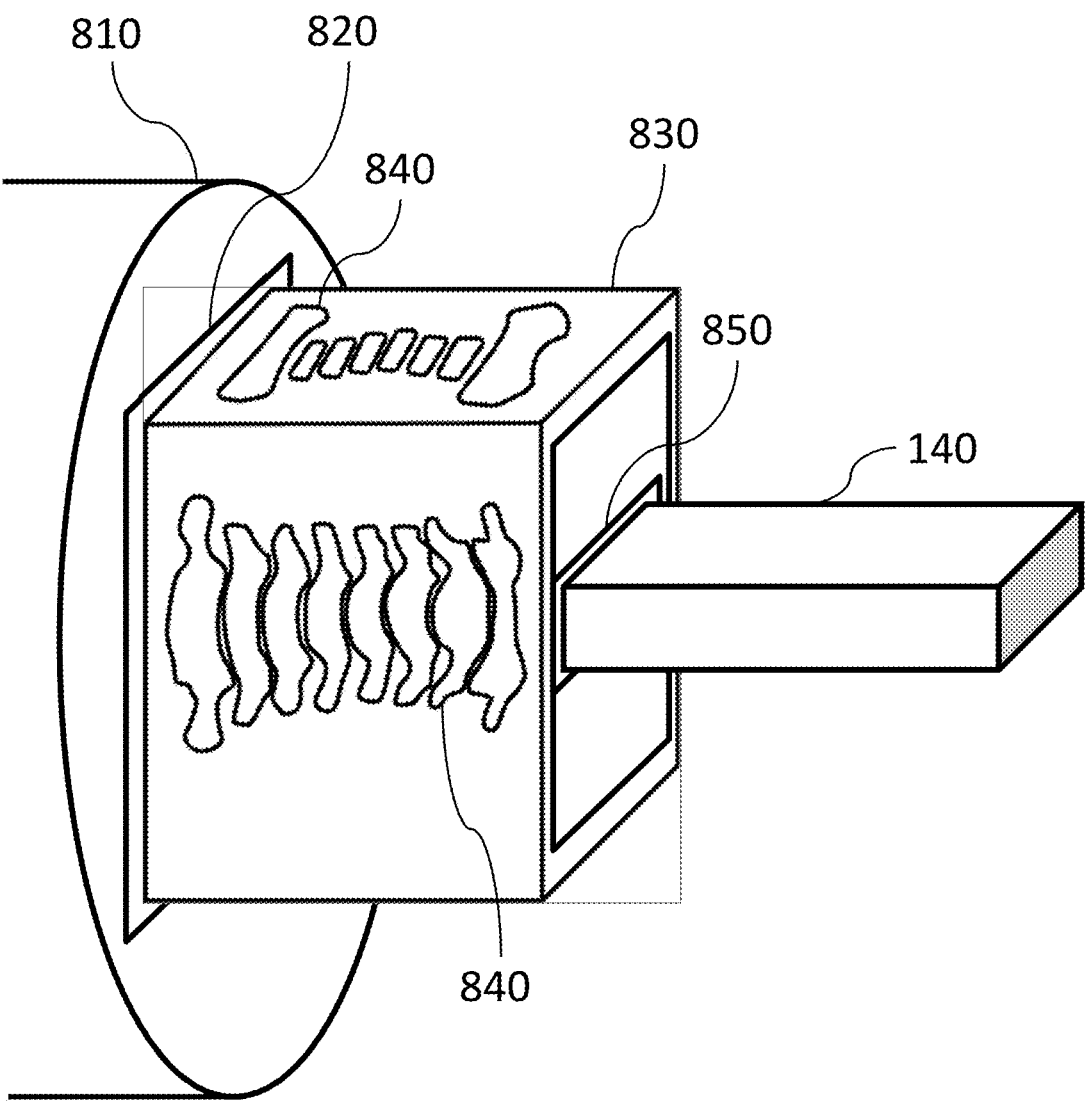
FIG. 8 is a diagram illustrating a simplified perspective view of an exemplary phantom system having a removable phantom attachment that can be inserted into a phantom for use with imaging systems relying on internal structure(s) for control of setup and/or delivery control in accordance with certain aspects of the present disclosure.

When the present disclosure refers to phantom "attachment," or the like, such contemplates direct attachment to a phantom (e.g., onto the housing depicted in FIGS. 1B, 1D and 2), attachment to a phantom via an intermediary such as a sheath (as depicted in FIGS. 3-7), or attachment via integration into a phantom insert (as depicted in FIG. 8).

Removable phantom attachments can be attached in a number of different ways. For example, a removable phantom attachment can be attached via pegs and holes, with magnets, etc. Some implementations may also include one or more positioning elements that provide for adjustment to the position or orientation of the removable phantom attachments. Positioning elements can include, for example, micrometer screws, tracks and guides, pivots, set screws, etc. Such removable phantom attachments may thus allow for modification of the phantom system without removing the phantom from its location on the patient couch. The removable nature of the disclosed phantom attachments can also permit the imaging of different anatomical features with the same phantom by utilizing different removable phantom attachments.

In some implementations, a removable phantom attachment can include one or more holder cavities configured to hold an infrared or RF transponder. Such transponders can be configured to transmit signals to a receiver to provide additional data for confirming or determining the orientation and/or position of the phantom. This can include, for example, triangulation, signal strength, etc.

In other implementations, the removable phantom attachment can include an external or internal anthropomorphic feature having a size or shape corresponding to what the external or internal at anthropomorphic feature would be on a child, on a person of below-average or above-average size, of a particular age, having a particular physical condition, etc. In other implementations, external or internal anthropomorphic features can be sized and shaped to correspond to a composite average of a patient anatomy represented by patients in a patient database.

Figure 2:
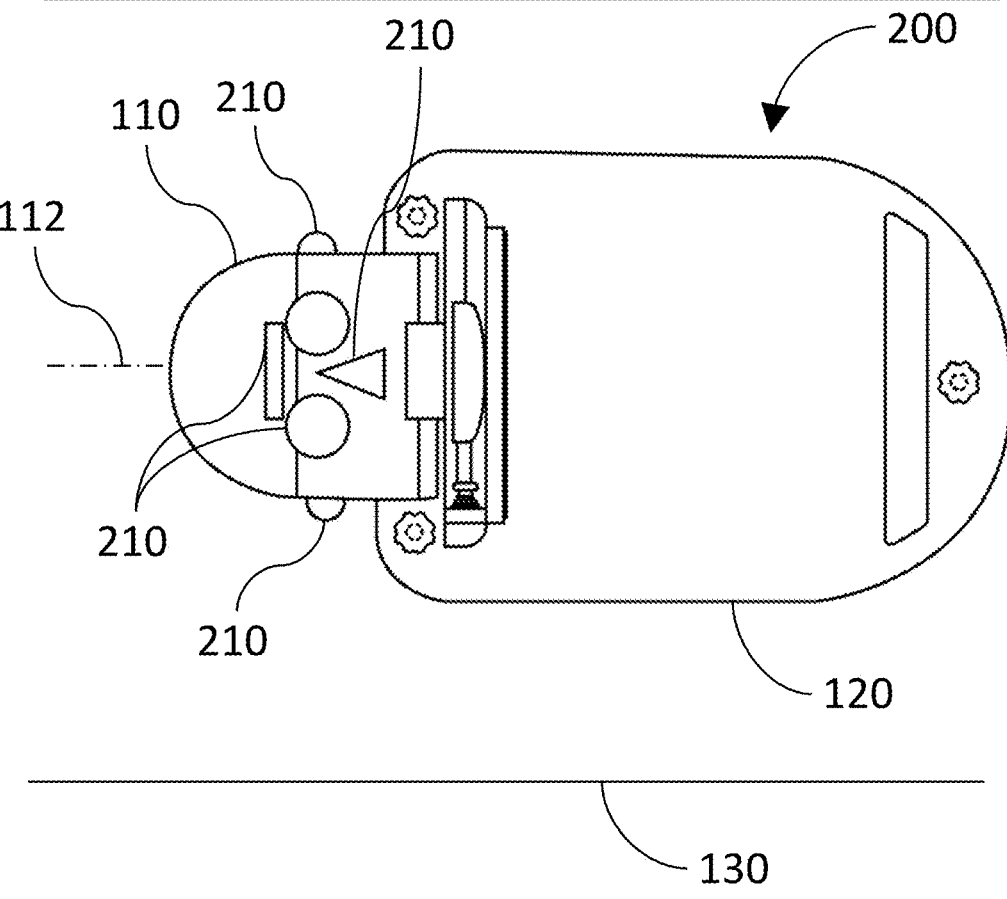
FIG. 2 is a diagram illustrating a simplified top view of an exemplary phantom system having external removable phantom attachments in accordance with certain aspects of the present disclosure.

FIG. 2 is a diagram illustrating a simplified top view of an exemplary phantom system having external removable phantom attachments. The specific embodiment depicted in FIG. 2 shows a number of removable phantom attachments 210 configured to be attached outside of the phantom 200, with the removable phantom attachments including an external anthropomorphic feature. The examples of external anthropomorphic features depicted in FIG. 2 include ocular cavities, a portion of a cranium just above the ocular cavities, a nose, and ears. In other implementations, external anthropomorphic features can include, for example, a mouth, a cranium, or an externally-visible portion of a chest region, a stomach region, a clavicle, a pelvis, or a vertebrae. In some embodiments, such removable phantom attachments can also include an internal anthropomorphic feature such as a nasal structure, ocular structure, or a mouth/throat structure. It is understood that while FIG. 2 depicts one exemplary combination of anthropomorphic features, no particular combination or feature is essential and various implementations can include any number or combination of anthropomorphic features as removable phantom attachments.

Figure 3:
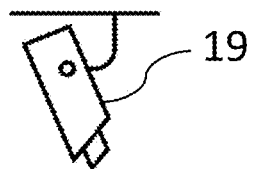
FIG. 3 is a diagram illustrating a simplified perspective view of an exemplary phantom system having an anthropomorphic sheath in accordance with certain aspects of the present disclosure.
Figure 3:
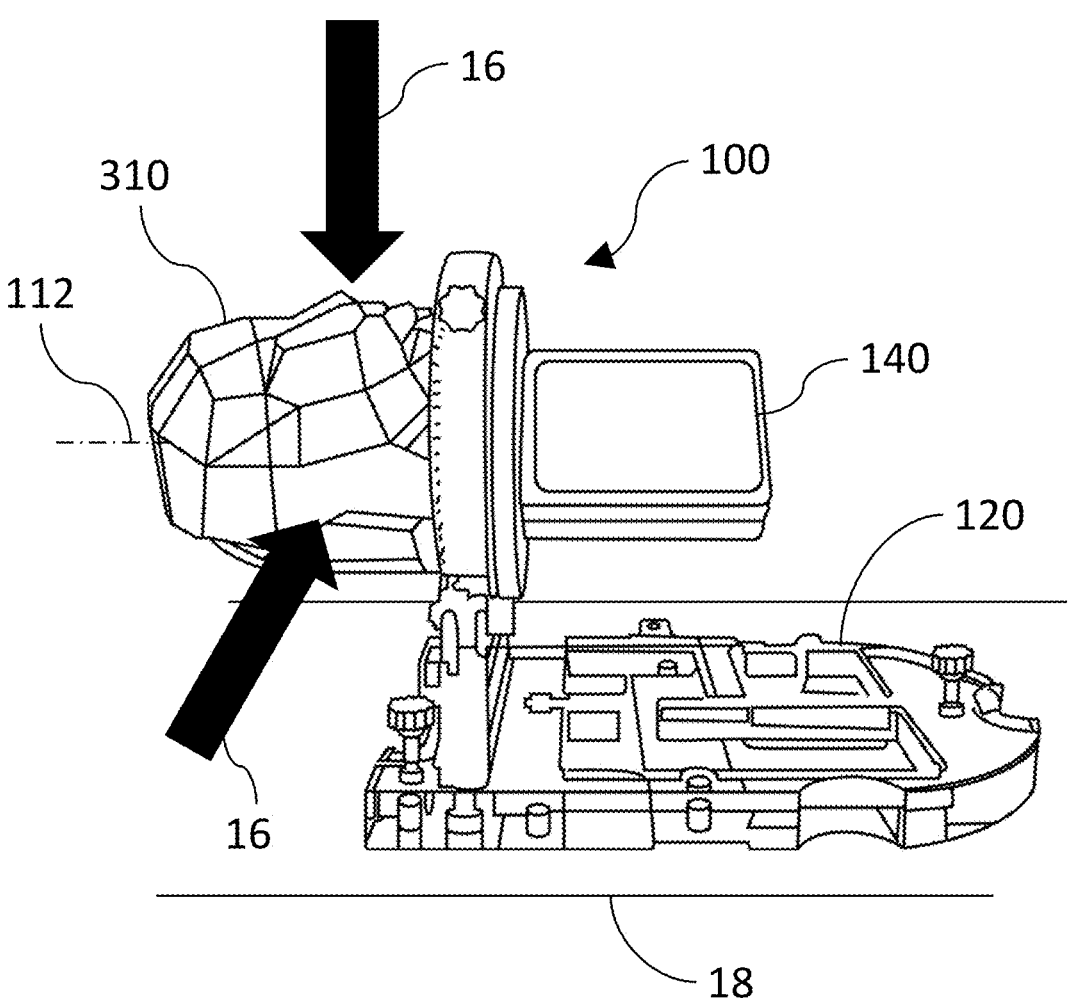

FIG. 3 is a diagram illustrating a simplified perspective view of an exemplary phantom system having an anthropomorphic sheath. In some embodiments, the removable phantom attachment can be an anthropomorphic sheath 310 configured to cover at least a portion of the phantom (e.g., phantom 110 as depicted in FIG. 1B).

The anthropomorphic sheath can be shaped to slide over phantom 110 and can be rigid or can be flexible with an elasticity to provide a secure fit. The anthropomorphic sheath may include one or more external and/or internal anthropomorphic features. For example, the anthropomorphic sheath can include external anthropomorphic features such as a nose, an ocular cavity, a mouth, a cranium, or an externally-visible portion of a clavicle, pelvis, or vertebrae. As previously discussed, certain implementations can include an anthropomorphic sheath that is shaped as an overall portion of a patient's anatomy. For example, an anthropomorphic sheath can be generally shaped to correspond to a portion of a head, an arm, a leg, a thorax, or a pelvic region.

In some embodiments, the anthropomorphic sheath may only have certain anthropomorphic features (e.g., ocular cavities, a nose, etc.). As such, certain implementations of the phantom system can also include additional removable phantom attachment(s) configured to be attached directly to the anthropomorphic sheath. Such additional removable phantom attachments can be similar to those described with reference to FIG. 2.

In other embodiments, the anthropomorphic sheath may have a thickness sufficient to contain one or more internal anthropomorphic features. For example, the anthropomorphic sheath can have a thickness of between 1.0 cm and 20 cm to permit inclusion of internal anthropomorphic feature(s), such as a nasal structure, ocular structure, or a mouth/throat structure.

Figure 4A:
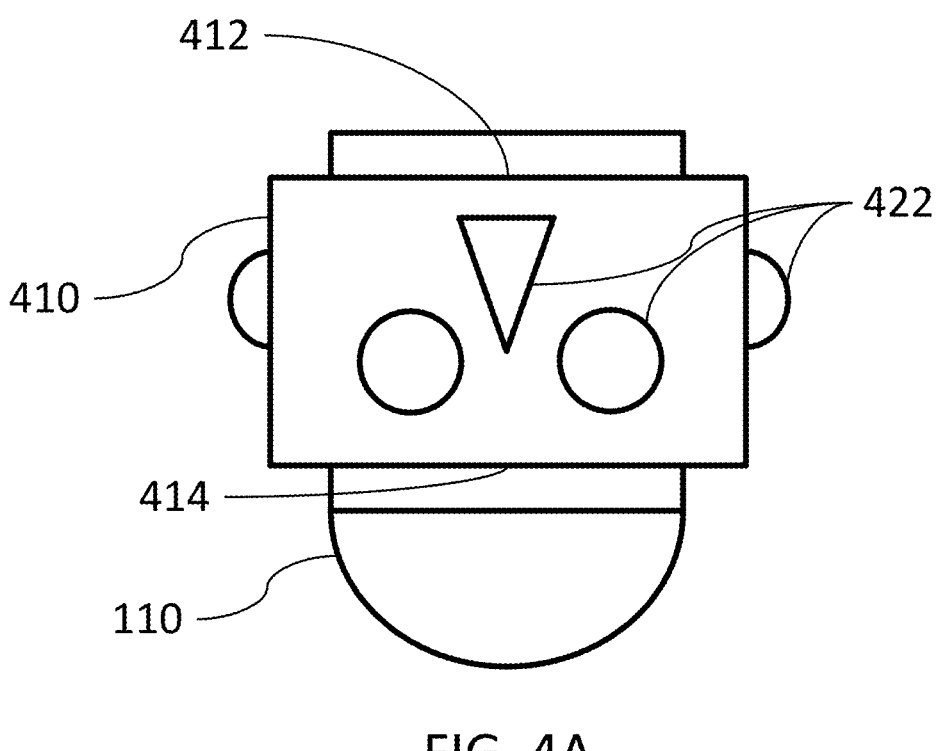
FIG. 4A is a diagram illustrating a simplified top view of an exemplary removable phantom attachment wrapping substantially around a phantom in accordance with certain aspects of the present disclosure.
Figure 4B:
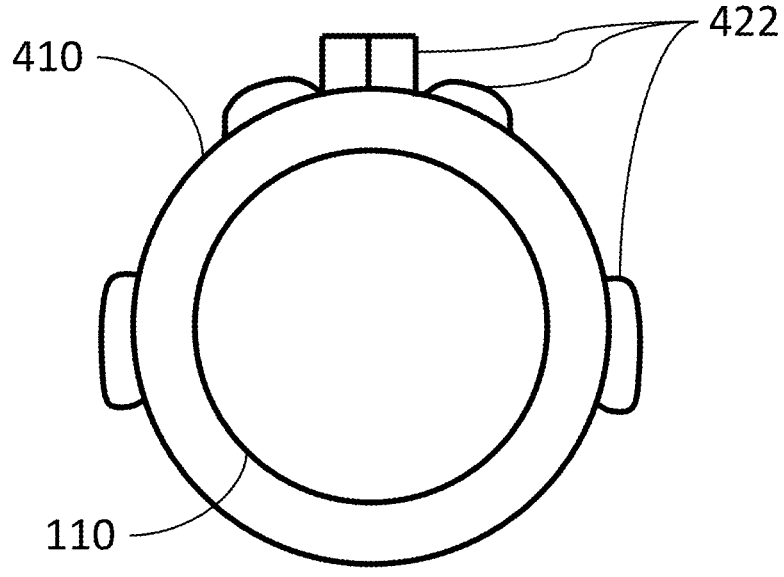
FIG. 4B is a diagram illustrating a simplified top view of the removable phantom attachment of FIG. 4A in accordance with certain aspects of the present disclosure.

FIG. 4A is a diagram illustrating a simplified top view of an exemplary removable phantom attachment wrapping substantially around a phantom. FIG. 4B is a diagram illustrating a simplified top view of the removable phantom attachment of FIG. 4A. In some embodiments, the removable phantom attachment can be a sheath configured to cover at least a portion of the phantom and include an external and/or internal anthropomorphic feature. Various examples of sheaths with anthropomorphic features are depicted in the embodiments of FIGS. 4A-7B. As depicted in FIGS. 4A/B, in one embodiment, sheath 410 can be configured to be a single piece that can be shaped to wrap substantially around the phantom 110. For example, such a sheath can be slipped over an accessible end of phantom 110. The sheath may be configured to wrap around the phantom by, for example, its shape (e.g., having a circular or rectangular cross section to match the operative part of the phantom), elasticity (e.g., being flexible to fit over a variety of phantom shapes), etc. As used herein, the term "substantially" with respect to wrapping around the phantom means that the sheath can encompass a complete cross-section (as shown in FIG. 4B) but may also encompass slightly less of the cross-section, for example, by having a split allowing a flexible sheath to be attached from another direction, such as slipped over the top of the phantom 110. While not intended to be specifically limiting, "substantially" can thus mean the sheath 410 can cover, for example, 80%, 90%, or 100% of the circumference of a phantom cross-section. Also, the term "around the phantom" refers to the operative part of the phantom where radiation is expected to be delivered or where imaging is expected to occur. Thus, "around the phantom" does not necessarily mean that the sheath covers the entire phantom (e.g., a base, electrical connections for radiation detectors, etc.).

To facilitate the placement of sheath 410 around phantom 110, some embodiments may have the sheath open at both ends (e.g., first end 412 and second end 414). Thus, it can be seen from FIG. 4A that sheath 410 can be slid over the exemplary phantom 110 for proper placement. While the embodiment of FIG. 4A is depicted with first end 412 and second end 414 open, it is contemplated that other embodiments may have one end closed (e.g., second end 414). Such an embodiment would be similar to the anthropomorphic sheath 310 of FIG. 3 but with the sheath 410 itself not necessarily having an anthropomorphic shape.

To allow the phantom attachment to facilitate QA for IGRT, the disclosed sheath embodiment of FIGS. 4A/B is depicted as having exemplary external anthropomorphic features. For any of the embodiments herein, the internal or external anthropomorphic features can be permanently attached or may be removably attached (similar to the embodiment of FIG. 2). Simplified examples of external anthropomorphic features 422 are depicted in FIGS. 4A/B as including eyes or ocular cavities, a nose, and ears. While the depicted anthropomorphic features are depicted with simplified representations, in any of the embodiments herein they may have varying levels of detail approximating real human anatomy (see, e.g., FIGS. 7C/D and 8 for additional examples).

Any of the disclosed anthropomorphic features can have physical shapes, imaging properties and/or radiation attenuation or scattering properties approximating what the feature would have in a real patient. Examples of materials to approximate for external and/or internal anthropomorphic features can include soft tissue, skin, fat, muscle, cartilage, water, or bone. It is contemplated that any combination of such anthropomorphic features may be included with any combination of the removable phantom attachments disclosed herein.

Figures 5A, 5B:
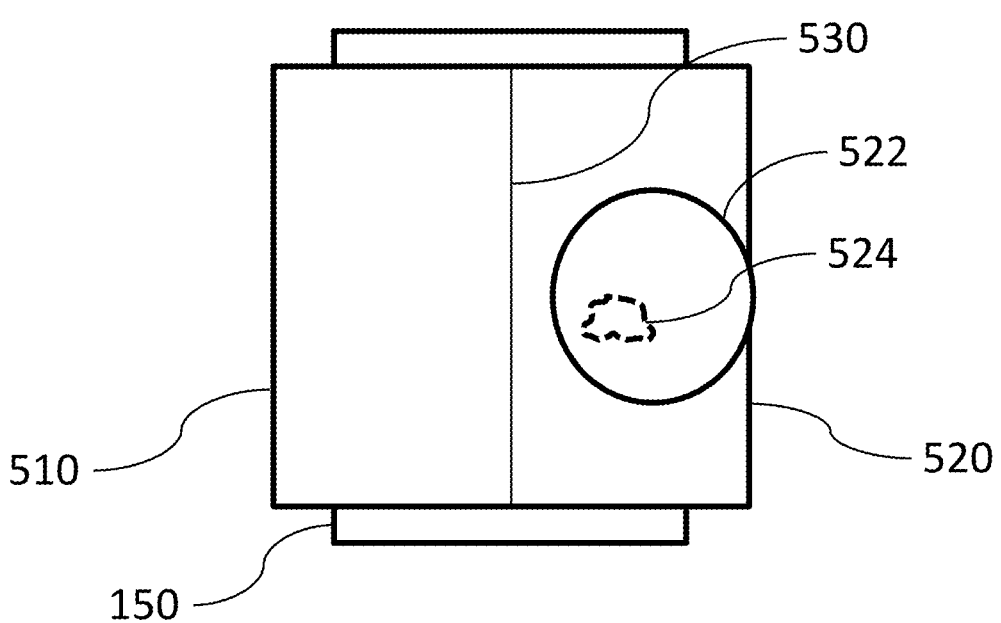
FIG. 5A is a diagram illustrating a simplified top view of an exemplary removable phantom attachment formed of multiple pieces in accordance with certain aspects of the present disclosure.
FIG. 5B is a diagram illustrating a simplified top view of the removable phantom attachment of FIG. 5A in accordance with certain aspects of the present disclosure.

FIG. 5A is a diagram illustrating a simplified top view of an exemplary removable phantom attachment formed of multiple pieces. FIG. 5B is a diagram illustrating a simplified top view of the removable phantom attachment of FIG. 5A. In some embodiments, the sheath can be configured to be multiple pieces shaped to wrap around the phantom. For example, the embodiment of FIGS. 5A/B depicts a removable phantom attachment comprising a first piece 510 and a second piece 520. The pieces (510, 520) can be configured to connect at one or more connection points 530 with one or more fasteners. Examples of such fasteners can include tabs and slots, hooks and loops, snaps, buckles, etc.

The embodiment of FIGS. 5-7 utilize phantom 150 as an exemplary phantom, which may be more suitable for anthropomorphic features associated with anatomy other than the patient's head. However, it is contemplated that any of the disclosed aspect in such embodiments can be utilized with any other phantom, e.g., phantom 110. In the example of FIG. 5A/B, first piece 510 does not have an anthropomorphic feature while second piece 520 does have anthropomorphic features. One example of an external anthropomorphic feature is depicted in FIGS. 5A/B as breast 522 that could be used to aid QA of SGRT. In some embodiments, as shown in FIG. 5A/B, breast 522 may include an internal anthropomorphic feature such as a simulated tumor 524 suitable for detection with internal imaging modalities (e.g., MM).

Figure 6A:
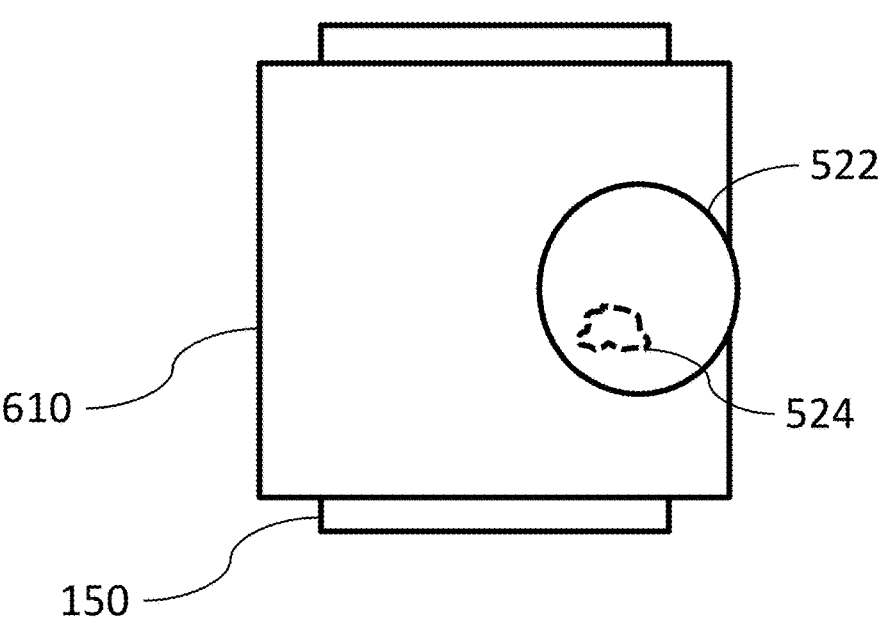
FIG. 6A is a diagram illustrating a simplified top view of an exemplary removable phantom attachment wrapping partially around a phantom in accordance with certain aspects of the present disclosure.
Figure 6B:
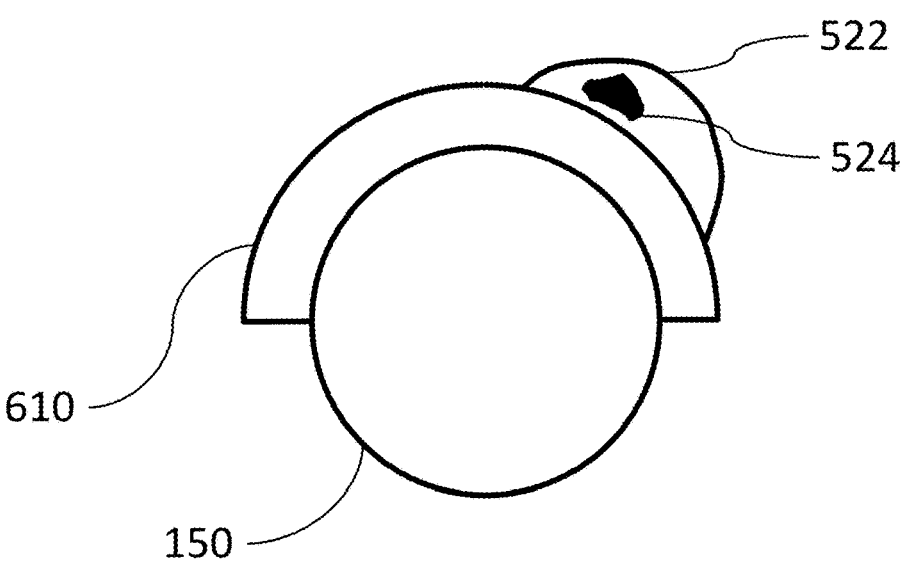
FIG. 6B is a diagram illustrating a simplified sectional view of the removable phantom attachment of FIG. 6A in accordance with certain aspects of the present disclosure.

FIG. 6A is a diagram illustrating a simplified top view of an exemplary removable phantom attachment wrapping partially around a phantom. FIG. 6B is a diagram illustrating a simplified top view of the removable phantom attachment of FIG. 6A. In some embodiments, the sheath 610 can be configured to wrap partially around the phantom. Similar to the embodiment of FIGS. 5A/B, sheath 610 has anthropomorphic features 522 and 524 but the sheath does not wrap substantially around phantom 150. Instead, sheath 610 can cover a smaller portion of phantom 150 (e.g., the top half) as shown in FIG. 6B. The depicted embodiment is exemplary and similar embodiments can wrap around other amounts of phantom 150 (e.g., 25%, 30%, 40%, 60%, 65%, etc.). To secure such embodiments, sheath 610 may be positioned at the top of the phantom such that it is balanced and would remain in place. In other cases, sheath 610 may be secured utilizing straps, adhesive, pins, or other similar mechanisms to removably but securely attach the sheath to the phantom in the desired position or orientation.

FIG. 7A is a diagram illustrating a simplified top view of an exemplary removable phantom attachment representing a change in patient weight. FIG. 7B is a diagram illustrating a simplified sectional view of the removable phantom attachment of FIG. 7A. In some embodiments, the removable phantom attachment can include an external or internal anthropomorphic feature having a size, shape, or location corresponding to what the external or internal anthropomorphic feature would be on a person that has undergone an increase or decrease in weight. For example, there may be a set of removable phantom attachments such as sheaths of varying sizes where the size or cross-section itself can be the anthropomorphic feature (e.g., a torso or hip region shape) indicative of a particular weight. FIGS. 7A/B show two examples of sheaths that represent an abdominal region. The depicted sheaths compare a larger sheath 710 (representing a patient at a greater weight) and a smaller sheath 720 (representing a patient at a lesser weight). Different-sized sheaths could also therefore have anthropomorphic features (e.g., ones representing tumors) at different locations with respect to the radiation delivery system. Utilizing various sized/shaped sheaths can thus facilitate QA of radiation delivery for patients that may undergo weight change. As seen, such weight changes could adversely affect treatment by changing patient registration for SGRT, changing radiation absorption, or having treatment targets or organs at risk be at different locations than expected. The concepts depicted in this embodiment may be combined with any of the disclosed embodiments herein, though would likely be most applicable to removable phantom attachments representing patient anatomy that is likely to undergo such changes (e.g., thorax, hips/waist, and legs) rather than more static portions of patient anatomy such as the head. Also, while some sheaths may have a simplified geometric design (e.g., a basic cylinder), some embodiments, such as the embodiment as shown in FIG. 7B, may have designs that more closely approximate human anatomical shapes.

FIG. 7C is a diagram illustrating a simplified top view of an exemplary removable phantom attachment that includes an internal anthropomorphic feature. FIG. 7D is a diagram illustrating a simplified sectional view of the removable phantom attachment of FIG. 7C. The location of the FIG. 7D sectional view is indicated in FIG. 7C by the horizontal dashed line. The removable phantom attachment of FIGS. 7C/D is similar to sheath 710 in FIGS. 7A/B but with the addition of internal anthropomorphic features 730, in this example, femoral heads and their associated acetabulum. This embodiment illustrates one example of how internal anthropomorphic features can be integrated into the material of any of the disclosed removable phantom attachments. In other embodiments, other internal anthropomorphic features may be utilized, for example, arteries, muscles, tendons, etc., as desired and as may be consistent with the portion of the patient anatomy that the removable phantom attachment is simulating.

To facilitate detection of removable phantom attachments by certain imaging devices (e.g., visible wavelength cameras), the surface of a removable phantom attachment can have a diffuse reflectivity of between 0.1 and 0.8 for light of wavelengths between 400 nm and 700 nm, or in some embodiments between 0.2 and 0.6 in this wavelength range. In other embodiments, such surfaces may have a diffuse reflectivity approximating that of human skin under ambient light in a clinical setting. In yet other embodiments, such as for removable phantom attachments that may be imaged with cameras or illumination sources operating outside the visible spectrum (e.g., IR at 700-1000 nm or UV at 100-400 nm), the diffuse reflectivity can also be between 0.1 and 0.8 for either/both of those wavelength ranges. Similar embodiments can also have a diffuse reflectivity of between 0.2 and 0.6 in those wavelength ranges. As reflectivity is the limit value of the reflectance, this means that reflectance depends on the thickness and shape of the object, while reflectivity is the intrinsic property of the material (measured as if it was a semi-infinite body).

FIG. 8 is a diagram illustrating a simplified perspective view of an exemplary phantom system having a removable phantom attachment that can be inserted into a phantom for use with imaging systems relying on internal structure for control of setup and/or delivery. As depicted in FIG. 8, certain embodiments of phantom 810 can have a cavity 820 and the removable phantom attachment 830 can be configured to be inserted into the cavity 820.

As also depicted in FIG. 8, the removable phantom attachment can include at least one internal anthropomorphic feature 840, for example, vertebrae. Thus, in various implementations, the internal anthropomorphic feature can be a skeletal portion shaped to represent a clavicle, a rib, a pelvis, or a vertebrae or may be a tissue portion shaped to represent a lung, a pancreas, a kidney, or a prostate, etc.

The internal anthropomorphic feature(s) may be imageable by a kV or MV X-ray system, a CT system, or an MRI system (e.g., by virtue of the materials used to form the feature(s)). Similar to the previously-described external anthropomorphic features, such internal anthropomorphic features can have a known shape and/or orientation that can be utilized in radiation therapy QA to monitor the orientation of the phantom and to provide more accurate radiation delivery to radiation detectors 140. As noted, some implementations of the phantom system can include radiation detectors, for example, a two-dimensional array of radiation detectors configured to be inserted into the cavity of the phantom. In the implementation shown in FIG. 8, the removable phantom attachment 830 may itself have a detector cavity 850 shaped to receive radiation detectors 140. In other embodiments, the phantom system can include point radiation detectors configured to be inserted into the cavity of the phantom. For example, such point radiation detectors can be diode or scintillator radiation detectors, typically of small size, to provide localized (e.g., an area of around 1 mm²) radiation measurements at specific points inside the phantom.

In the following, further features, characteristics, and exemplary technical solutions of the present disclosure will be described in terms of items that may be optionally claimed in any combination:

Item 1: A phantom system comprising a phantom; and a removable phantom attachment configured to be attached to the phantom so that the phantom system has an identifiable orientation and/or location to an imaging device.

Item 2: The phantom system of any of Item 1, wherein the removable phantom attachment comprises an external and/or internal anthropomorphic feature at least partially formed of a material having a density approximating water, tissue, bone, lung, or air.

Item 3: The phantom system of any of the preceding Items, further comprising a two-dimensional array of radiation detectors configured to be inserted into the phantom.

Item 4: The phantom system of any of the preceding Items, the removable phantom attachment configured to be attached outside of the phantom and including an external anthropomorphic feature.

Item 5: The phantom system of any of the preceding Items, wherein the external anthropomorphic feature is a nose, an ocular cavity, a mouth, a cranium, or an externally-visible portion of a clavicle, a pelvis, or a vertebrae.

Item 6: The phantom system of any of the preceding Items, the removable phantom attachment further including an internal anthropomorphic feature.

Item 7: The phantom system of any of the preceding Items, wherein the internal anthropomorphic feature is a nasal structure, ocular structure, or a mouth/throat structure.

Item 8: The phantom system of any of the preceding Items, wherein the removable phantom attachment is an anthropomorphic sheath configured to cover at least a portion of the phantom and including an external and/or internal anthropomorphic feature.

Item 9: The phantom system of any of the preceding Items, wherein the anthropomorphic sheath includes an external anthropomorphic feature selected from the group consisting of a nose, an ocular cavity, a mouth, a cranium, or an externally-visible portion of a chest region, a stomach region, a clavicle, pelvis, or vertebrae.

Item 10: The phantom system of any of the preceding Items, wherein the anthropomorphic sheath is generally shaped to correspond to a portion of a head, an arm, a leg, a thorax, or a pelvic region.

Item 11: The phantom system of any of the preceding Items, further comprising an additional removable phantom attachment configured to be attached directly to the anthropomorphic sheath.

Item 12: The phantom system of any of the preceding Items, wherein the sheath has a thickness of between 1.0 cm and 20 cm and includes an internal anthropomorphic feature.

Item 13: The phantom system of any of the preceding Items, wherein the removable phantom attachment is a sheath configured to cover at least a portion of the phantom and including an external and/or internal anthropomorphic feature.

Item 14: The phantom system of any of the preceding Items, wherein the sheath is configured to be a single piece that is shaped to wrap substantially around the phantom.

Item 15: The phantom system of any of the preceding Items, wherein the sheath is configured to be a plurality of pieces shaped to wrap around the phantom, the plurality of pieces configured to connect at one or more connection points with one or more fasteners.

Item 16: The phantom system of any of the preceding Items, wherein the sheath is configured to wrap partially around the phantom.

Item 17: The phantom system of any of the preceding Items, wherein the removable phantom attachment comprises an external or internal anthropomorphic feature having a size, shape, or location corresponding to what the external or internal anthropomorphic feature would be on a person that has undergone an increase or decrease in weight.

Item 18: The phantom system of any of the preceding Items, wherein the phantom has a cavity and the removable phantom attachment is configured to be inserted into the cavity.

Item 19: The phantom system of any of the preceding Items, the removable phantom attachment comprising at least one internal anthropomorphic feature.

Item 20: The phantom system of any of the preceding Items, wherein the internal anthropomorphic feature is a skeletal portion shaped to represent a clavicle, a rib, a pelvis, or a vertebrae or is a tissue portion shaped to represent a lung, a pancreas, a kidney, or a prostate.

Item 21: The phantom system of any of the preceding Items, wherein the internal anthropomorphic feature is able to be imaged by a kV or MV X-ray system, a CT system, or an MRI system.

Item 22: The phantom system of any of the preceding Items, further comprising a two-dimensional array of radiation detectors configured to be inserted into the cavity of the phantom.

Item 23: The phantom system of any of the preceding Items, further comprising one or more point radiation detectors configured to be inserted into the cavity of the phantom.

Item 24: The phantom system of any of the preceding Items, wherein the removable phantom attachment comprises an external or internal anthropomorphic feature having a size or shape corresponding to what the external or internal at anthropomorphic feature would be on a child.

Item 25: The phantom system of any of the preceding Items, wherein the removable phantom attachment is attached to the phantom via pegs and holes.

Item 26: The phantom system of any of the preceding Items, wherein the removable phantom attachment is attached to the phantom via magnets.

Item 27: The phantom system of any of the preceding Items, the removable phantom attachment further comprising one or more positioning elements that provide for adjustment to a position or orientation of the removable phantom attachment.

Item 28: The phantom system of any of the preceding Items, the removable phantom attachment further comprising one or more holder cavities configured to hold an infrared or RF transponder.

Item 29: The phantom system of any of the preceding Items, wherein a surface of the removable phantom attachment has a diffuse reflectivity of between 0.1 and 0.8 for light of wavelengths between 400 nm and 700 nm.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

The invention claimed is:

1. A phantom system comprising: a phantom; and
a removable phantom attachment configured to be attached to the phantom so that the phantom system has an identifiable orientation and/or location to an imaging device, the removable phantom attachment comprising an external and/or internal anthropomorphic feature with a shape configured for orienting and/or locating the phantom system.

2. The phantom system of claim 1, wherein the external and/or internal anthropomorphic feature is at least partially formed of a material having a density approximating water, tissue, bone, lung, or air.

3. The phantom system of claim 1, the removable phantom attachment configured to be attached outside of the phantom.

4. The phantom system of claim 3, wherein the external anthropomorphic feature is a nose, an ocular cavity, a mouth, a cranium, or an externally-visible portion of a clavicle, a pelvis, or a vertebra.

5. The phantom system of claim 1, wherein the removable phantom attachment is an anthropomorphic sheath configured to cover at least a portion of the phantom.

6. The phantom system of claim 5, further comprising an additional removable phantom attachment configured to be attached directly to the anthropomorphic sheath.

7. The phantom system of claim 5, wherein the sheath has a thickness of between 1.0 cm and 20 cm and includes an internal anthropomorphic feature.

8. The phantom system of claim 1, wherein the removable phantom attachment is a sheath configured to cover at least a portion of the phantom and configured for removable attachment of an external and/or internal anthropomorphic feature.

9. The phantom system of claim 8, wherein the sheath is configured to be a single piece that is shaped to wrap substantially around the phantom.

10. The phantom system of claim 8, wherein the sheath is configured to be a plurality of pieces shaped to wrap around the phantom, the plurality of pieces configured to connect at one or more connection points with one or more fasteners.

11. The phantom system of claim 8, wherein the sheath is configured to wrap partially around the phantom.

12. The phantom system of claim 1, wherein the external or internal anthropomorphic feature has a size, shape, or location corresponding to what the external or internal anthropomorphic feature would be on a person that has undergone an increase or decrease in weight.

13. The phantom system of claim 1, wherein the removable phantom attachment comprises an external or internal anthropomorphic feature having a size or shape corresponding to what the external or internal at anthropomorphic feature would be on a child.

14. The phantom system of claim 1, wherein a surface of the removable phantom attachment has a diffuse reflectivity of between 0.1 and 0.8 for light of wavelengths between 400 nm and 700 nm.

* * * * *